(12) United States Patent
Cushman et al.

(10) Patent No.: US 6,569,897 B1
(45) Date of Patent: May 27, 2003

(54) ALKENYLDIARYLMETHANE NON-NUCLEOSIDE HIV-1 REVERSE TRANSCRIPTASE INHIBITORS

(75) Inventors: Mark S. Cushman, West Lafayette, IN (US); Agustin Casimiro-Garcia, West Lafayette, IN (US); William G. Rice, Frederick, MD (US)

(73) Assignees: Purdue Research Foundation, West Lafayette, IN (US); The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/581,927

(22) PCT Filed: Jan. 15, 1999

(86) PCT No.: PCT/US99/00916

§ 371 (c)(1),
(2), (4) Date: Jun. 19, 2000

(87) PCT Pub. No.: WO99/36384

PCT Pub. Date: Jul. 22, 1999

Related U.S. Application Data

(60) Provisional application No. 60/071,700, filed on Jan. 16, 1998.

(51) Int. Cl.[7] .................. A61K 31/216; C07C 69/76
(52) U.S. Cl. ................................... 514/506; 560/57
(58) Field of Search ......................... 560/57; 514/506

(56) References Cited

U.S. PATENT DOCUMENTS 5,439,899 A * 8/1995 Cushman et al. ........... 514/169

OTHER PUBLICATIONS

Cushman, M. et al. (1996): J. Med. Chem. vol. 39, 3217–3227.*
Casimiro–Garcia, A. et al. (1999): J. Med. Chem. vol. 42, 4861–4874.*
Buckheit Jr. et al., "Comparative anti–HIV evaluation of diverse HIV–1–specific reverse transcriptase inhibitor–resistant virus isolates demonstrates the existence of distinct phenotypic subgroups", Antiviral Res., 26, pp. 117–132, (1995).
Rice et al., "Inhibitors of HIV Nucleocapsid Protein Zinc Fingers as Candidates for the Treatment of Aids", Science, vol. 270, pp 1194–1197 (1995).
Rice et al., "The site of antiviral action of 3–nitrosobenzamide on the infectivity process of human immunodeficiency virus in human lymphocytes", Proc. Natl. Acad. Sci. U.S.A., vol. 90, pp 9721–9724, (1993).
Ciminale et al., "A Bioassay for HIV–1 Based on Env–CD4 Interaction", Aids Research and Human Retroviruses, vol. 6, pp 1281–1287, (1990).
Orlek et al., "Comparison of Azabicyclic Esters and Oxadiazoles as Ligands for the Muscarinic Receptor", J. Med. Chem., vol. 34, pp 2726–2735, (1991).
Yousif, "The Reaction of Carboxylic Acid Chlorides with O,O–Dialkyldithiophosphoric Acids", Phos. Sulfur Silicon., vol. 46, pp. 79–81, (1989).
Barbero et al., "Simple Procedures for the Hydrolysis of Trimethyl Trithioorthocarboxylates to Methyl Thiolcarboxylates. A Convenient Route to Electron–Rich Aromatic and Heteroaromatic Methyl Thiolcarboxylates", Synthesis, pp 300–302, (1988).
Willmore et al., "Diels–Alder Reactions of α–Substituted Styrenes with ρ–Benzoquinone", J. Org. Chem., vol. 59, pp. 1889–1891, (1994).
Herkes et al. "Fluoro Olefins. I. The Synthesis of β–Substituted Perfluoro Olefins", J. Am. Chem. Soc., vol. 89, pp. 1311–1318 (1967).
Pine et al., "Carbonyl Methylenation Using a Titanium–Aluminum (Tebbe) Complex", J. Org. Chem, vol. 50, p. 1212, (1985).
Saunders et al., "Novel–Quinuclidine–Based Ligands for the Muscarinic Cholinergic Receptor", J. Med. Chem., vol. 33, pp. 1128–1138, (1990).
Sauerberg et al., "Novel Functional $M_1$ Selective Muscarinic Agonists. Synthesis and Structure–Activity Relationships of 3–(1,2,5–Thiadiazolyl)–1,2,5, 6–tetrahydro–1–methylpyridines", J. Med. Chem., vol. 35, pp. 2274–2283, (1992).
Moltzen, et al., "Bioisosteres of Arecoline: 1,2,3,6,–Tetrahydro–5–pyridyl–Substituted and 3–Piperidyl–Substituted Derivatives of Tetrazoles and 1,2,3–Triazoles. Synthesis and Muscarinic Activity", J. Med. Chem, vol. 37, pp. 4085–4099, (1994).
Friary et al., "A Direct Preparation of 3–Hydroxy–1,2–benzisoxasoles", J. Het. Chem., vol. 25(16), pp. 1277–1278, (1979).

* cited by examiner

Primary Examiner—Alan L. Rotman
Assistant Examiner—Golam M. M. Shameem
(74) Attorney, Agent, or Firm—Barnes & Thornburg

(57) ABSTRACT

Alkenyldiarylmethane (ADAM) compounds have been found effective as anti-HIV agents. Novel ADAM compounds, their pharmaceutical formulations and a method of using same to treat viral infections are described.

6 Claims, No Drawings

ALKENYLDIARYLMETHANE NON-NUCLEOSIDE HIV-1 REVERSE TRANSCRIPTASE INHIBITORS

CROSS-REFERENCES TO RELATED APPLICATIONS

This application is a U.S. national application of international application serial No. PCT/US99/00916 filed Jan. 15, 1999, which claims priority to U.S. provisional application serial No. 60/071,700 filed Jan. 16, 1998.

GOVERNMENT RIGHTS

This invention was made with support of funds provided under Grant No. A1-36624 awarded by the National Institutes of Health. The United States Government has certain rights in the invention.

FIELD OF THE INVENTION

This invention relates to compounds useful for antiviral applications. More particularly, this invention relates to non-nucleoside HIV-1 reverse transcriptase inhibitors having a common alkenyldiarylmethane structure.

BACKGROUND AND SUMMARY OF THE INVENTION

The non-nucleoside HIV-1 reverse transcriptase inhibitors (NNRTIs) are a structurally diverse set of compounds that inhibit reverse transcriptase by an allosteric mechanism involving binding to a site adjacent to the deoxyribonucleoside triphosphate binding site of the enzyme. Familiar examples of NNRTIs include hydroxyethoxymethylphenylthiothymine (HEPT), tetrahydroimidazobenzodiazepinone (TIBO), dipyridodiazepinone (nevirapine), pyridinone, bis(heteroaryl)piperazine (BHAP), tertbutyldimethylsilylspiroaminooxathiole dioxide (TSAO), and α-anilinophenylacetamide (α-APA) derivatives. Nevirapine has recently been approved for clinical use as an anti-AIDS agent.

The use of NNRTIs as anti-AIDs agents has been limited by the development of viral resistance to the NNRTIs. Although the rapid emergence of resistant viral strains has hampered the clinical development of the NNRTIs for the treatment of AIDS, several strategies have emerged for overcoming resistance, including switching to another NNRTI to which the virus has remained sensitive, using higher doses of the NNRTI against the resistant strain, employing of combinations of agents which elicit mutations that counteract one another, and combining NNRTIs with nucleoside reverse transcriptase inhibitors (RTIs). Accordingly, a need remains for additional NNRTIs having unique patterns of resistance mutations in order to facilitate the application of these strategies.

The synthesis and biological evaluation of NNRTIs in the alkenyldiarylmethane (ADAM) series has recently been reported. Several of the alkenyldiarylmethane compounds were disclosed as inhibiting the cytopathic effect of a wide variety of HIV-1 strains in CEM, MT-4, and monocyte-macrophage cultures. (Cushman et al. *J. Med. Chem* 1996, 39, 3217–3227) The most potent of these disclosed compounds was ADAM I (1), which displayed anti-HIV activity vs. a wide range of HIV-1 isolates and was synergistic with AZT. However, the potency of ADAM I (1) against a variety of non-resistant HIV-1 strains was lower than that generally observed with many of the known NNRTIs, ranging from 0.56 μM vs. HIV-$1_{65}$ in MT-4 cells to 151 μM vs. HIV-$1_{N119}$ in MT-4 cells.

The present invention is directed to a series of ADAM I related compounds that are inhibitors of reverse transcriptase activity and inhibit the cytopathic activity of HIV strains.

DETAILED DESCRIPTION OF THE INVENTION

The design of additional alkenyldiarylmethanes has been aided by the availability of X-ray structures of HIV-1 reverse transcriptase complexed with nevirapine, α-APA, and TIBO. These structures reveal that nevirapine, α-APA, and TIBO assume a similar butterfly shape and bind to the enzyme in a similar manner with considerable overlap. Analysis of the X-ray crystallography structures allows the construction of a hypothetical model of the binding of ADAM I (1) to HIV-1 RT. The model was constructed by overlapping the structure of ADAM I (1) with that of nevirapine (2) in the binding pocket of HIV-1 RT (Sculpt® 2.0, Interactive Simulations, San Diego, Calif.). During this process, it was assumed that the hexenyl side chain of ADAM I (1) would point in the same direction as the cyclopropyl substituent of nevirapine. The nevirapine structure was then removed, the structure of the protein "frozen", and the energy of the complex minimized while allowing the ligand to move. The resulting hypothetical structure was consistent with the reported structures of NNRTI enzyme complexes, and was also supported by prior mutagenesis studies of the alkenyldiarylmethane binding site of HIV-1 reverse transcriptase, in which it was determined that the resistance mutations to ADAM 1 circumscribe a well-defined binding pocket.

According to the model generated by this analysis, the end of the ADAM I (1) side chain occupies a cavity formed by Glu 138, Lys 103, Tyr 181, and Val 179 of the HIV-1 RT. Several functional groups are present that would be capable of hydrogen bonding, including the phenolic hydroxyl group of Tyr 181, the backbone amide and side chain carboxylate of Glu 138, and the terminal amino group of Lys 103. It was anticipated that the incorporation of functional groups at the end of the alkenyl chain of the ligand which are capable of hydrogen bonding might allow favorable interactions with the adjacent residues of the RT. Therefore, alkenyldiarylmethane related compounds were synthesized to incorporate functionalities at the end of the alkenyl side chain that would be capable of hydrogen bonding.

The present invention is directed to non-nucleoside compounds that inhibit reverse transcriptase activity, their pharmaceutical compositions and methods utilizing such compounds/compositions for treating patients suffering from a viral infection. More particularly the compounds of the present invention are useful for treating patients suffering from a disease of retroviral origin, such as AIDs.

The compounds of the present invention are alkenyldiarylmethane compounds of formula I:

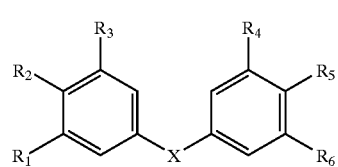

wherein X is selected from the group consisting of

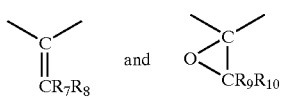

wherein $R_1$ and $R_6$ are H or halo;

$R_2$ and $R_5$ are independently $OR_{11}$;

$R_3$ and $R_4$ are $CO_2R_{12}$ or Z; or $R_2$ and $R_3$ taken together with the carbon atoms ($C_2$, $C_3$) to which they are attached and $R_4$ and $R_5$ taken together with the carbon atoms ($C_4$, $C_5$) to which they are attached form a 5- or 6-membered ring of the formula

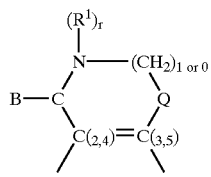

wherein Q is O, S, or Se;

$R^1$ is $C_1$–$C_4$ alkyl,

B is —$OR^1$ or =O, and r is 1 or 0;

provided that when B is =O, r is 1 and bond a is a single bond and when B is —$OR^1$, r is 0 and bond a is a double bond;

$R_7$ is hydrogen;

$R_8$ is selected from the group consisting of $(CH_2)_mOR_{13}$, $(CH_2)_mN_3$, $(CH_2)_mCOOR_{14}$, $(CH_2)_mZ$, and $(CH_2)_mNH_2$;

$R_9$ and $R_{10}$ are independently selected from the group consisting of H, ($C_1$–$C_5$) alkyl, $(CH_2)_nOR_{13}$, $(CH_2)_nN_3$, $(CH_2)_nCOOR_{14}$, $(CH_2)_mZ$ and $(CH_2)_nNH_2$;

$R_{11}$, $R_{12}$, $R_{13}$ and $R_{14}$ are independently selected from the group consisting of H and ($C_1$–$C_5$) alkyl; m is 1–4; n is 0–4: and Z is selected from the following subtituent groups:

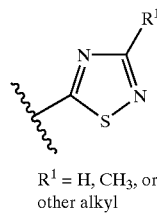

$R^1$ = H, $CH_3$, or other alkyl

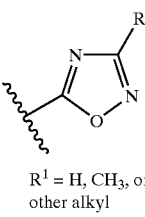

$R^1$ = H, $CH_3$, or other alkyl

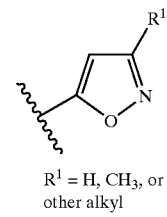

$R^1$ = H, $CH_3$, or other alkyl

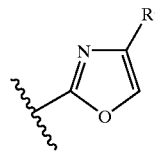

$R^1$ = H, $CH_3$, or other alkyl

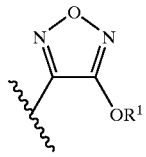

$R^1$ = H, $CH_3$, or other alkyl

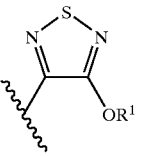

$R^1$ = H, $CH_3$, or other alkyl

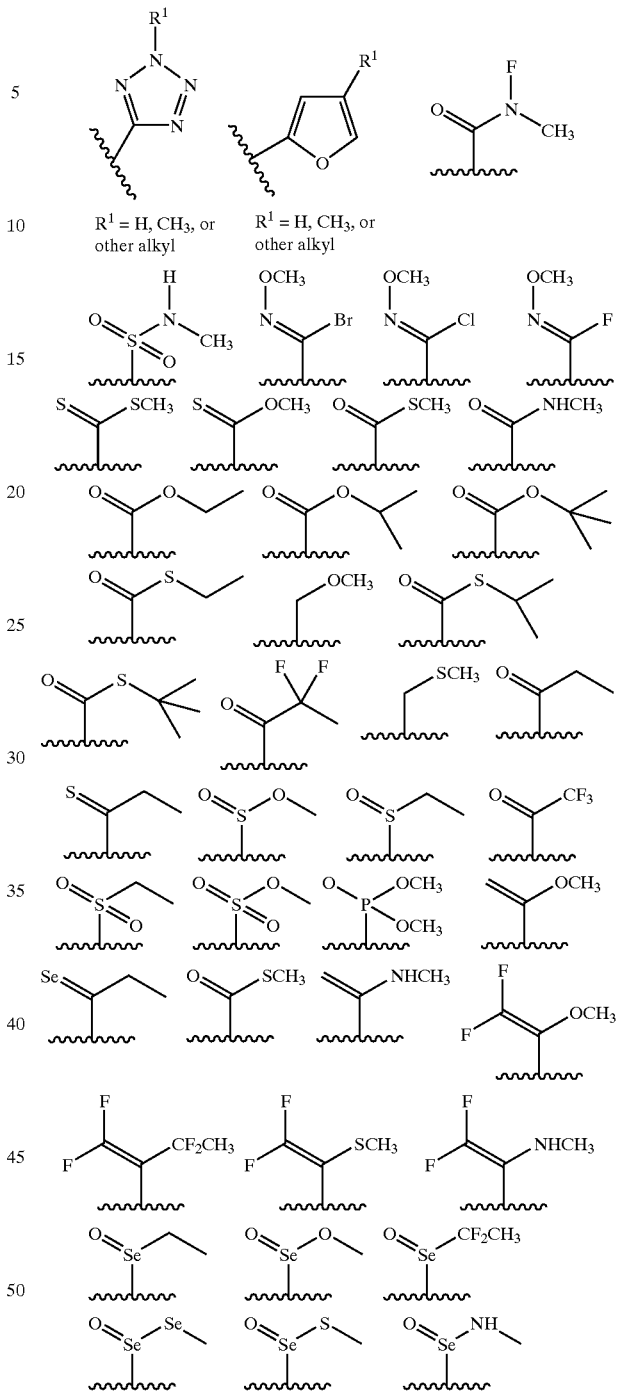

with the proviso that when X is

$R_8$ is not $(CH_2)_2OH$.

In one embodiment of this invention there is provided a compound of the above formula I, wherein X is

$R_1$ and $R_6$ are independently Br or Cl, $R_2$ and $R_5$ are each $OCH_3$, $R_3$ and $R_4$ are each $CO_2CH_3$ or Z, $R_7$ is H and $R_8$ is $(CH_2)_mOH$, $(CH_2)_mCOOCH_3$, $(CH_2)_mZ$, or $(CH_2)_mN_3$, wherein m is 2 or 3. These compounds inhibit the cytopathic effect of HIV-$1_{RF}$ in CEM-SS cells. (See Table 1 below).

In another embodiment of this invention there is provided a reverse transcriptase inhibiting compound of the above formula I wherein X is

$R_1$ and $R_6$ are halo;

$R_2$ and $R_5$ are $OCH_3$;

$R_3$ and $R_4$ are $CO_2CH_3$;

$R_7$ is H;

$R_8$ is $(C_2-C_5)$ alkyl, $(CH_2)_mOR_{13}$, $(CH_2)_mN_3$, $(CH_2)_mCOOR_{14}$, $(CH_2)_mZ$, and $(CH_2)_mNH_3$;

$R_{13}$ and $R_{14}$ are independently selected from the group consisting of H and $(C_1-C_5)$ alkyl; and m is 2–4.

In still another embodiment of the invention $R_1$ and $R_6$ are both chloro or bromo.

The compounds of this invention are readily formulated into pharmaceutical compositions, also within the scope of this invention, for use in the presently described method for treatment of patients suffering from a disease of retroviral origin. In one embodiment of this invention, the pharmaceutical composition comprises a reverse transcriptase inhibitory effective amount of a compound of formula I:

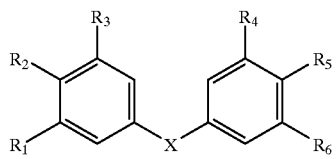

I wherein X is selected from the group consisting of

 and 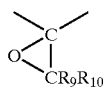

wherein $R_1$ and $R_6$ are H or halo;

$R_2$ and $R_5$ are independently $OR_{11}$;

$R_3$ and $R_4$ are $CO_2R_{12}$ or Z; or $R_2$ and $R_3$ taken together with the carbon atoms ($C_2$, $C_3$) to which they are attached and $R_4$ and $R_5$ taken together with the carbon atoms ($C_4$, $C_5$) to which they are attached form a 5- or 6-membered ring of the formula

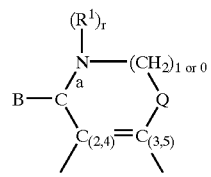

wherein Q is O, S, or Se;

$R^1$ is $C_1-C_4$ alkyl,

B is $-OR^1$ or $=O$, and r is 1 or 0;

provided that when B is $=O$, r is 1, and bond a is a single bond, and when B is $-OR^1$, r is 0 and bond a is a double bond;

$R_7$ is hydrogen;

$R_8$ is selected from the group consisting of $(CH_2)_mOR_{13}$, $(CH_2)_mN_3$, $(CH_2)_mCOOR_{14}$, $(CH_2)_mZ$, and $(CH_2)_mNH_2$;

$R_9$ and $R_{10}$ are independently selected from the group consisting of H, $(C_1-C_5)$ alkyl, $(CH_2)_nOR_{13}$, $(CH_2)_nN_3$, $(CH_2)_nCOOR_{14}$, $(CH_2)_mZ$ and $(CH_2)_nNH_2$;

$R_{11}$, $R_{12}$, $R_{13}$ and $R_{14}$ are independently selected from the group consisting of H and $(C_1-C_5)$ alkyl; m is 1–4; n is 0–4 and Z is as defined above; and a pharmaceutically acceptable carrier.

Another pharmaceutical composition within the scope of this invention comprises a reverse transcriptase inhibiting compound of the above formula I wherein X is

$R_1$ and $R_6$ are halo;

$R_2$ and $R_5$ are $OCH_3$, $R_3$ and $R_4$ are $CO_2CH_3$ or Z;

$R_8$ is $(C_2-C_4)$ alkyl, $(CH_2)_mOR_{13}$, $(CH_2)_mN_3$, $(CH_2)_mCOOR_{14}$, $(CH_2)_mZ$ and $(CH_2)_mNH_3$;

$R_{13}$ and $R_{14}$ are independently selected from the group consisting of H and $(C_1-C_5)$ alkyl; and m is 2 or 3, and a pharmaceutically acceptable carrier.

The present invention further provides pharmaceutical formulations comprising an effective amount of an alkenyldiarylmethane compound for use in the present method for treating a patient suffering from a disease of retroviral origin. As used herein, an effective amount of the alkenyldiarylmethane compound is defined as the amount of the compound which, upon administration to a patient, alleviates or eliminates symptoms of the disease, or reduces or eliminates detectable levels of the virus in the treated patient.

The effective amount to be administered to a patient is typically based on body surface area, patient weight, patient condition, and the potency, efficacy and therapeutic index of the compound being administered. Body surface area may be approximately determined from patient height and weight (see e.g., Scientific Tables, Geigy Pharmaceuticals, Ardley, N.Y., pages 537–538 (1970)). Effective doses will vary, as recognized by those skilled in the art, dependent on route of administration, excipient usage and the possibility of co-usage with other therapeutic treatments including other anti-viral agents.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one aspect of the present embodiment, the alkenyldiarylmethane compound is dissolved in a saline solution containing 5% of dimethyl sulfoxide and 10% Cremphor EL (Sigma Chemical Company). Additional solubilizing agents well-known to those familiar with the art can be utilized as pharmaceutical excipients for delivery of the present compounds.

The present compounds can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active compound and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and conventional fillers and tableting agents.

Typically, oral dosage levels range from 50–500 mg per dose, administered from 1 to 4 times per day. More typically, oral dosage levels ranging from 100 to 250 mg/dose are administered 1 to 4 times per day. With respect to parenteral dosing, levels between 25 and 250 mg are typically administered 1 to 4 times per day. Dosing regimens with lower or higher amounts of drug may be indicated depending upon the patients clinical state and the potency of the compound being administered.

The anti-viral activity of the described compounds was measured utilizing two different assays. The first assay measures the effectiveness of the alkenyldiarylmethane compound to inhibit reverse transcriptase activity, and the second assay measured the compound's ability to inhibit the cytopathic activity of HIV-1 to cells cultured in vitro. The mechanism of action for the disclosed compounds' antiviral activities is believed to be due at least in part to the compounds' ability to inhibit reverse transcriptase (RT) activity. Several of the disclosed ADAM compounds have an inhibitory effect on RT and yet do not exhibit a detectable inhibitory effect on viral cytopathicity in the HIV cell assay. This may be the result of the failure of the compound to penetrate the cell membrane. For example, compound 21 has activity as an RT inhibitor and yet no detectable inhibitory cytopathic effect was detected. The inactivity of 21 might possibly be due to the fact that the amino group is protonated at the pH of the assay medium and therefore should be less able to penetrate cellular membranes. Such compounds may have utility as antiviral agents, if they can be formulated as prodrugs, using techniques known to those skilled in the art, or through the use of other techniques that are known to increase cellular uptake of compounds.

The following examples are provided to illustrate various embodiments of the invention and are not intended to in any way limit the scope of the invention as set forth in this specification and appended claims.

EXAMPLE 1

Preparation of Congeners of Compound 1

Congeners of 1 were prepared in which the effect of alkenyl chain length on activity could be investigated. Various analogs were also prepared in which the bromines present in 1 were replaced by chlorines, iodines, and hydrogens.

Considering first the compounds having the same substitution in the aromatic rings as in 1, compounds 3–7 were prepared from the inter-mediate benzophenone 10. The methylene and ethylene compounds 3 and 4 were prepared by the Wittig reactions of 10 starting from methyltriphenylphosphonium bromide and ethyltriphenylphosphonium bromide, respectively, using sodium bis(trimethylsilyl) amide as the base. The methoxyethylene congener 5 was prepared in a similar reaction employing methoxymethyl (triphenyl)phosphonium bromide. Similarly, reaction of ketone 10 with the Wittig reagent derived from 3-[tert-(butyldiphenylsilyloxy)propyl]triphenylphosphonium bromide afforded intermediate 6. Removal of the protecting group from 6 was accomplished with tetra-n-butylammonium fluoride in THF, yielding the alcohol 7. Reaction of the alcohol 7 with mesyl chloride in the presence of triethylamine gave the mesylate 8, which was converted to the azide 9 on treatment with sodium azide in DMF.

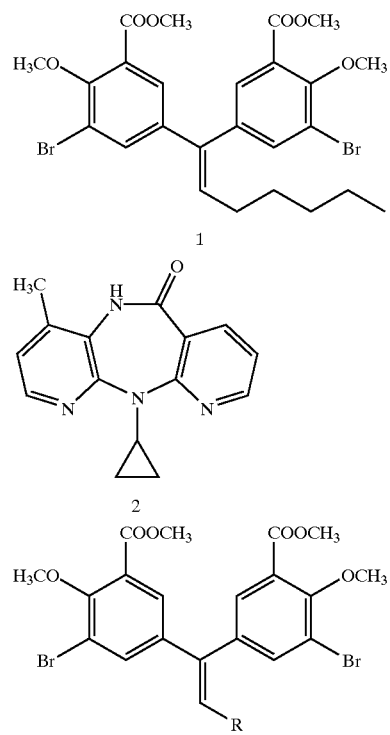

3  R = H
4  R = CH$_3$
5  R = OCH$_3$
6  R = CH$_2$CH$_2$OTBDPS
7  R = CH$_2$CH$_2$OH
8  R = CH$_2$CH$_2$OSO$_2$CH$_3$
9  R = CH$_2$CH$_2$N$_3$

-continued

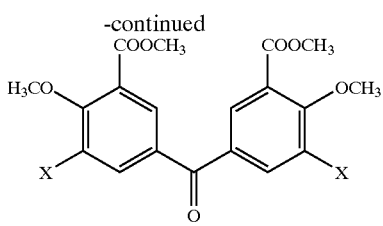

10 X = Br
11 X = Cl

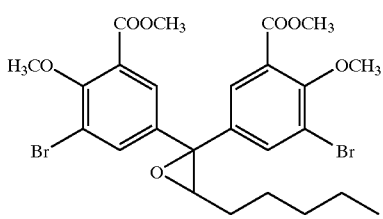

12

In order to convert 1 into a closely related compound bearing a reactive functionality which might serve to alkylate the enzyme, the conversion of the alkene moiety to an epoxide was considered. Reaction of 1 with m-chloroperoxybenzoic acid in methylene chloride afforded the desired epoxide 12.

A series of dichloro alkenyldiarylmethanes 13–23 bearing alkenyl substituents capable of hydrogen bonding was prepared using the substituted dichlorobenzophenone 11 as the starting material. Using the Horner-Emmons reaction, compound 24 was reacted with NaH at low temperature for 1 h to produce the corresponding anion, which was then reacted with ketone 11 to afford, after purification, ester 13 in good yield. The required reagent 24 was prepared from diethylphosphonoacetic acid (25) and 2-(trimethylsilyl)ethanol (26). Deprotection of 13 was carried out with tetra-n-butylammonium fluoride in THF, affording the carboxylic acid 14 as a colorless crystalline solid. The methyl ester 15 and tert-butyl ester 16 were also prepared by the Horner-Emmons reaction starting from methyl diethylphosphonoacetate (27) and tert-butyl diethylphosphonoacetate (28), respectively.

The Wittig reaction of the ketone 11 with the ylide derived from 3-[tert(butyldiphenylsilyloxy)propyl]triphenylphosphonium bromide afforded the alkene 17. Removal of the tert-butyldiphenylsilyl protecting group was accomplished with tetra-n-butylammonium fluoride in THF to provide the alcohol 18. Oxidation of 18 under Jones conditions (CrO$_3$, sulfuric acid, acetone), followed by extraction with 3 M aqueous sodium hydroxide, yielded the tricarboxylic acid 23, resulting from oxidation of the primary alcohol in 18 and hydrolysis of the two ester groups during extraction. On the other hand, reaction of the alcohol 18 with methanesulfonyl chloride in dichloromethane, using triethylamine as the base, afforded the mesylate 19. Reaction of the mesylate 19 with sodium azide in DMF gave the azide 20.

Various methods were considered for the reduction of the azide 20 to the amine 21. The usual methods for conversion of azides to amines involving lithium aluminum hydride or catalytic hydrogenations are obviously not suitable for accomplishing the conversion of 20 to 21 because of the other functionality in addition to the azide present in 20. Following a protocol described by Brown and Salunkhe,

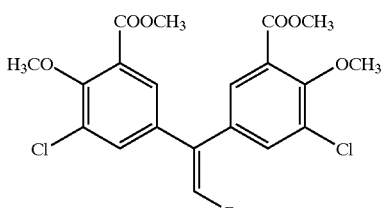

13 R = COOCH$_2$CH$_2$TMS
14 R = COOH
15 R = COOCH$_3$
16 R = COOC(CH$_3$)$_3$
17 R = CH$_2$CH$_2$OTBDPS
18 R = CH$_2$CH$_2$OH
19 R = CH$_2$CH$_2$OSO$_2$CH$_3$
20 R = CH$_2$CH$_2$N$_3$
21 R = CH$_2$CH$_2$NH$_2$
22 R = CH$_2$CH$_2$CH$_2$COOCH$_3$

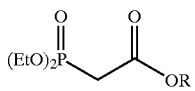

24 R = CH$_2$CH$_2$TMS
25 R = H
27 R = CH$_3$
28 R = C(CH$_3$)$_3$

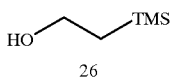

26

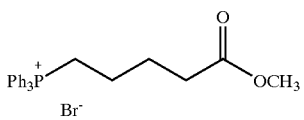

29

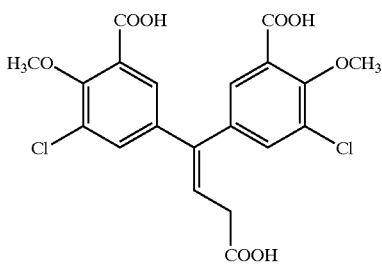

23

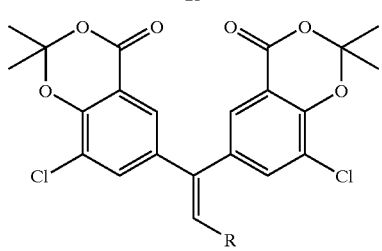

30 R = CH$_2$CH$_2$OH
31 R = CH$_2$CH$_2$Br

-continued

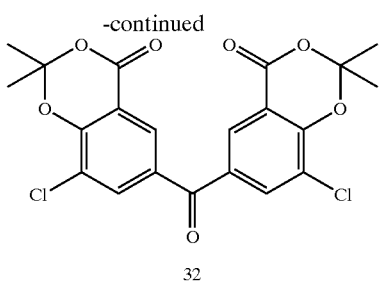

32

(*Tetrahedron Lett*. 1995, 36, 7987–7990) compound 20 was reacted with dichloroborane dimethyl sulfide complex to produce, after appropriate work up, amine 21 in low yield (15%). Dichloroborane dimethyl sulfide complex has been reported to react with olefins, but this process has been described to be slow and incomplete in the absence of trichloroborane. However, it is likely that the reactivity of the borane complex with olefins is at least in part responsible for the poor yield observed in the conversion of 20 to amine 21. Alternative methods were then considered in order to reduce 20 to 21 in acceptable yield. Zwierzak et al. reported the preparation of amines from azides using a variant of the Staudinger reaction. (*Synthesis*, 1985, 202–204) They reacted organic azides with trialkyl phosphates, instead of the commonly used triphenylphosphine, to produce iminophosphorane intermediates, which after treatment with hydrogen chloride afforded the corresponding amine hydrochlorides. The higher reactivity of trialkyl phosphates towards azides was the main assumption for the modification. This methodology was considered to be the most adequate for the conversion of azide 20 to amine 21, since the other reactive functionality present in 21 would not be affected by this method. In fact, the reaction of azide 20 with triethylphosphite for 24 h, followed by hydrolysis of the intermediate iminophosphorane with dry hydrogen chloride for 48 h, afforded the amine 21 as its hydrochloride salt in 86% yield.

In order to synthesize an alkenyldiarylmethane having a terminal methoxycarbonyl group at the end of an extended alkenyl side chain, the benzophenone 11 was subjected to a Wittig reaction with the ylide derived from the reaction of the phosphonium bromide 29 with sodium bis (nimethylsilyl)amide in THF. This resulted in the formation of the desired compound 22, referred to herein as ADAM II.

The effect of replacement of the methoxycarbonyl and methyl ether groups by cyclic acetonides on biological activity could be readily investigated by evaluating the known alcohol 30, prepared previously from the ketone 32. The primary alcohol was converted to the corresponding bromide 31 with carbon tetrabromide and triphenylphosphine in acetonitrile.

In order to determine the importance of the two halogen atoms for biological activity, congeners of ADAM I (1) were prepared in which the halogens were replaced by iodines and by hydrogens. The syntheses of these compounds is outlined in Scheme 1. Treatment of the known diphenylmethane 33 with dimethylsulfate in refluxing acetone with potassium carbonate as the base resulted in methylation of both carboxylic acids and both phenols to afford compound 34, which was oxidized to the benzophenone 35 with chromium trioxide in acetic anhydride. Reaction of the ketone present in 35 with the Wittig reagent derived from n-hexyltriphenylphosphonium bromide gave the desired analog 36, in which the two chlorines present in 1 have been replaced by hydrogens.

Scheme 1[a]

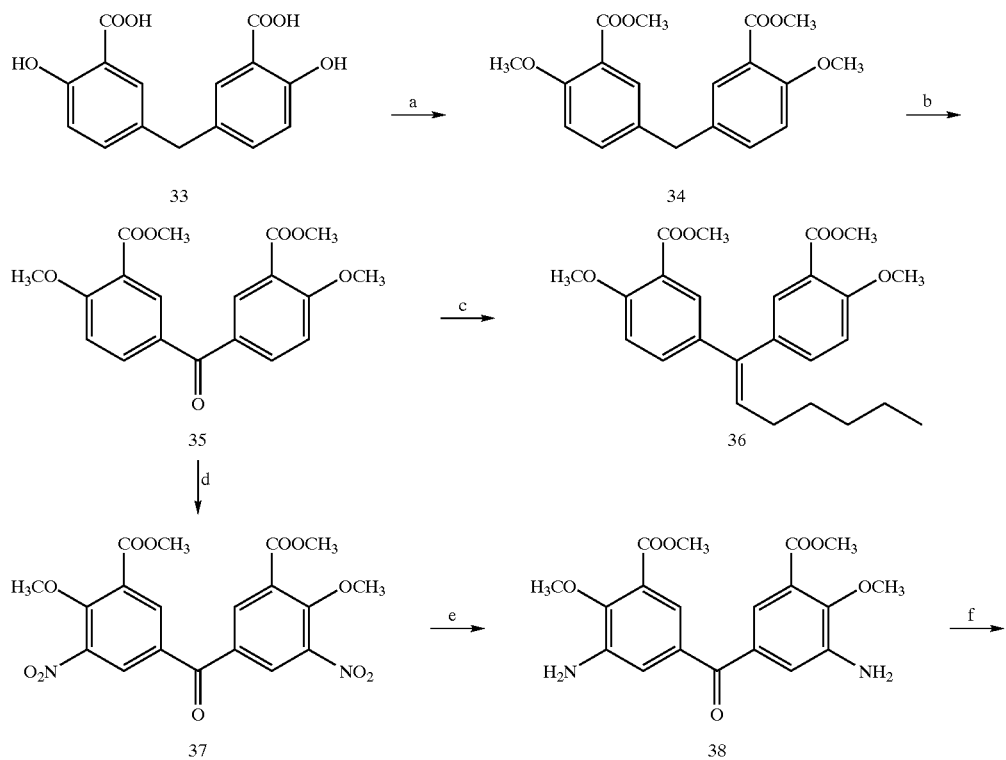

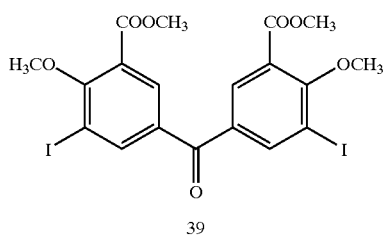

39

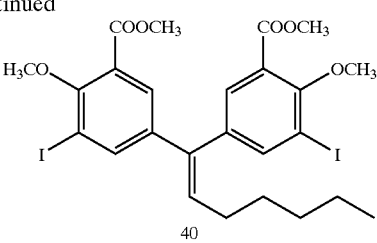

40

[a]Reagents: (a) Me₂SO₄, K₂CO₃, Me₂CO, reflux (6 h); (b) CrO₃, Ac₂O, 0° C. (1 h) and RT (12 h); (c) (1) n-C₆H₁₃PPh₃Br, NaN(SiMe₃)₂, THF, 0° C. (30 min), (2) add 35, 23° C. (12 h); (d) HNO₃, Ac₂O, RT (12 h); (e) H₂, PtO₂, EtOAc; (f) (1) NaONO, HCl, H₂O, 30 min (0° C.), (2) I₂, KI, H₂O, RT (30 min); (g) (1) n-C₆H₁₃PPh₃Br, NaN(SiMe₃)₂, THF, 0° C. (30 min), (2) add 39, 23° C. (12 h).

Nitration of 35 with nitric acid in acetic anhydride afforded the dinitro intermediate 37. The two nitro groups present in 37 were reduced to amines with Adam's catalyst in ethyl acetate to provide the diamino compound 38. Treatment of the diamine 38 with nitrous acid resulted in the conversion of both amines to diazonium groups, which were displaced by iodide in the presence of potassium iodide and iodine under aqueous conditions to provide intermediate 39. The reaction of 39 with the ylide derived from n-hexyltriphenylphosphonium bromide afforded the desired analog 40.

EXAMPLE 2

Biological Results

Nineteen new alkenyldiarylmethanes were tested for prevention of the cytopathic effect of HIV-1$_{RF}$ in CEM-SS cells and for cytotoxicity in uninfected CEM-SS, and the results are listed in Table 1. In addition, they were tested as inhibitors of HIV-1 reverse transcriptase, and the resulting IC$_{50}$ values are also listed in Table 1. The most potent of the new alkenyldiarylmethanes, as well as the one with the highest therapeutic index, proved to be ADAM II (22), which displayed an EC$_{50}$ for prevention of the cytopathic effect of HIV-1$_{RF}$ of 0.013 μM. This represents an approximately 700-fold increase in potency over the lead compound 1, which was the most potent alkenyldiarylmethane of the previously disclosed ADAM series. Perhaps more importantly, the therapeutic index (the ratio of the CC$_{50}$ value to the EC$_{50}$ value) increased by a factor of 162. The other new compounds which were equipotent or more potent than 1 for the prevention of HIV-1 cytopathicity included the primary alcohol 7 (EC$_{50}$=6.0 μM), the azide 9 (EC$_{50}$=1.1 μM), the primary alcohol 18 (EC$_{50}$=8.6 μM), and the azide 20 (EC$_{50}$=0.27 μM). No inhibitory effect was detected for the remaining novel alkenyldiarylmethanes tested for inhibition of HIV-1 cytopathicity at concentrations up to those resulting in cytotoxicity in uninfected cells (see Table 1).

TABLE 1

Anti-HIV-1 Activities of ADAMs.

| compd | RT (IC$_{50}$ μM)[a] | XTT Assay EC$_{50}$ (μM)[b] | CC$_{50}$ (μM)[c] | TI[d] |
|---|---|---|---|---|
| 1 | 0.38 | 9.2 | 138 | 15 |
| 3 | >100 | NA[e] | 316 | — |
| 4 | 26 | NA | 10 | — |
| 5 | >100 | NA | 22 | — |
| 7 | 31.6 | 6.0 | >316 | >52 |
| 9 | 94 | 1.1 | >316 | >278 |

TABLE 1-continued

Anti-HIV-1 Activities of ADAMs.

| compd | RT (IC$_{50}$ μM)[a] | XTT Assay EC$_{50}$ (μM)[b] | CC$_{50}$ (μM)[c] | TI[d] |
|---|---|---|---|---|
| 12 | 5.6 | NA | >100 | — |
| 14 | >100 | NA | 48 | — |
| 15 | 16 | NA | 25 | — |
| 16 | >100 | NA | >100 | — |
| 18 | >100 | 8.6 | 16.8 | 2 |
| 19 | 96 | NA | 6.9 | — |
| 20 | 2.0 | 0.27 | 41.8 | 155 |
| 21 | 63 | NA | 15 | — |
| 22 | 0.3 | 0.013 | 31.6 | 2430 |
| 23 | >100 | NA | >316 | — |
| 30 | >100 | NA | 18.8 | — |
| 31 | >100 | NA | 176 | — |
| 36 | 3.2 | NA | 14 | — |
| 40 | 11 | NA | >316 | — |

[a]Inhibitory activity vs. HIV-1 reverse transcriptase with rCdG as the template-primer.
[b]The EC$_{50}$ is the 50% inhibitory concentration for cytopathicity of HIV-1$_{RF}$ in CEM-SS cells.
[c]The CC$_{50}$ is the 50% cytotoxic concentration for mock-infected CEM cells.
[d]The TI is the therapeuric index, which is the CC$_{50}$ divided by the EC$_{50}$.
[e]NA means there was no observed inhibition of HIV-1 cytopathicity up to the cytotoxic concentration in uninfected cells.

The observed increase in antiviral potency of 22 relative to 1 did not correlate with inhibition of HIV-1 RT with poly(rC).oligo(dG) as the template primer, since 1 (IC$_{50}$ vs. RT=0.38 μM) was essentially equipotent as an enzyme inhibitor than ADAM II (22) (IC$_{50}$ vs. RT=0.30 μM). All of the new compounds displaying anti-HIV activity were also less potent than 1 as inhibitors of HIV-1 RT with poly(rC).oligo(dG) as the template primer, and some of them were significantly less active. Examples include compounds 7 (IC$_{50}$ vs. RT>31.6 μM), 9 (IC$_{50}$ vs. RT=94 μM), and 18 (IC$_{50}$ vs. RT>100 μM). Conversely, analogs 12 and 36 inhibit HIV-1 RT with IC$_{50}$ values of 5.6 μM and 3.2 μM, respectively, and are inactive as inhibitors of HIV-1 mediated cytopathogenic effect.

Some of the closely related structural analogs of 1 are revealing in their inactivity as inhibitors of the cytopathic effect of HIV-1. Examples include the epoxide 12, the dechlorinated analog 36, and the diiodo congener 40. These inactive compounds emphasize the fact that there is a relatively high degree of structural specificity associated with the antiviral activity of the compounds in the series, so that even small changes in structure can result in complete loss of activity. The inactivity of 36 and 40 emphasize a significant role played by the two bromine atoms present in 1. In this regard, the dichloro analog 41 was reported previously to retain activity, although it was approximately half as potent as 1. However, the effect of bromine vs.

chlorine substitution is not always consistent. For example, if one considers the bromo alcohol 7 ($EC_{50}$ 6.0 $\mu$M) vs. the chloro alcohol 18 ($EC_{50}$ of 8.6 $\mu$M), they are approximately equipotent as inhibitors of viral cytopathicity. On the other hand, the chloro azide 20 ($EC_{50}$ 0.27 $\mu$M) is four times more potent than the bromo azide 9 ($EC_{50}$ 1.1 $\mu$M), The effect of replacement of the methoxycarbonyl and methyl ether groups by cyclic acetonides can be seen by comparison of the activities of the primary alcohols 18 and 30. While 18 inhibited the cytopathic effect of HIV-$1_{RF}$ with an $EC_{50}$ of 8.6, the cyclic acetonide 30 was inactive. The corresponding primary bromide 31 was also inactive.

There appears to be an important effect of chain length of the alkenyl appendage. Both of the active azides 9 and 20 have a chain length which is identical with the alkenyl chain present in ADAM 1, and in the most active compound, ADAM II (22), the chain length is only slightly longer.

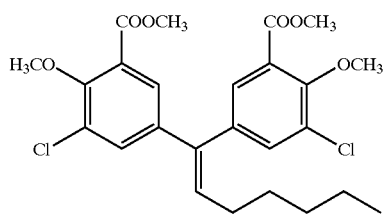

41

The effect of incorporation of hydrogen bonding groups at the end of the alkenyl chain seems to be variable, depending on the specific group incorporated and the length of the chain. For example, the primary alcohol 18 was effective in preventing the cytopathic effect of HIV-$1_{RF}$ with an $EC_{50}$ of 8.6 $\mu$M, but the corresponding amine 21 was inactive at 100 $\mu$M. The most effective compounds for inhibition of viral cytopathicity were ADAM II (22), having a methyl ester at the end of the chain, and the two azides 9 and 20. Although these compounds do have hydrogen bond accepting groups at the end of the alkenyl chain, it is difficult to attribute their greater antiviral activity to a greater affinity for the enzyme, because they are not more potent than 1 as enzyme inhibitors, at least with poly(rC.oligo(dG) as the template-primer.

In order to determine whether or not ADAM II was indeed acting as an NNRTI compound 22 was tested in a number of assays representative of important events in the replication cycle of HIV-1. These included (in addition to RT inhibition with poly(rA).oligo(dT) and poly(rC).oligo(dG) as template primers), assays for inhibition of HIV-1 attachment/fusion to target cells and the activities of HIV-1 integrase and protease enzymes. The effect of the compound on nucleocapsid protein was also investigated. Compound 22 did not have any significant effect on integrase, protease, or nucleocapsid protein. (See Table 2). However, it inhibited RT with either poly(rA).oligo(dT) or poly(rC).oligo(dG) as template primers. The greater sensitivity to inhibition with poly(rC).oligo (dG) as the template/primer is characteristic of the HIV-1-specific non-nucleoside reverse transcriptase inhibitors. Interestingly, ADAM I 1, which had an $IC_{50}$ of 0.38 $\mu$M with poly(rC).oligo(dG) as the template primer did not inhibit the enzyme with poly(rA).oligo(dT) as the template-primer. Thus there exists a clear distinction between the abilities of ADAM I and ADAM II to inhibit RT activity with the poly(rA).oligo(dT) template primer system.

In addition to the molecular target-based mechanistic assays, ADAM II (22) was also evaluated in a time course assay to determine the site of action of the compound during the early phase of HIV-1 replication, as well as with latently HIV-1 infected U1 cells to probe for any antiviral actions during the post-infective late phase of viral replication. The profile of inhibition of ADAM II corresponded to that of an NNRTI, in which antiviral activity was diminished when the compound was added to cultures four hours after initiation of infection. This is analogous to the effects of nevirapine, but unlike the action of dextran sulfate, which blocks virus attachment at the cell surface and loses its effectiveness within the first half hour after initiation of infection. PCR-based analysis confirmed that ADAM II prevented formation of proviral DNA during the early phase of infection. ADAM II had no effect on virus production from U1 cells induced with TNF-$\alpha$ to produce virus from integrated proviral DNA. Thus, ADAM II acted biologically to inhibit replication by preventing reverse transcription.

The scope of the anti-HIV activity of ADAM II was investigated in a number of laboratory-adapted strains, lymphocyte-tropic clinical isolates, clade representatives, and monocyte-tropic strains of HIV-1. Likewise, ADAM II was tested for inhibitory activity against an array of HIV-1 strains containing mutations in the reverse transcriptase enzyme. (See Tables 3, 4 and 5). The mutant viruses were obtained either by in vitro biological selection in the presence of various NNRTIs, or by site directed mutagenesis. In order to preserve continuity of data across the surfeit of virus strains, a greater amount of virus (higher MOI) was used in these competitive studies than was used in the original screening assays. For this reason, the $EC_{50}$ was generally about 20-fold greater in these studies than in the original screen. Nevertheless, ADAM II retained potent anti-HIV-1 activity against a wide variety of laboratory and clinical HIV-1 strains in CEM-SS, PBMC, and Mono/Mac cells (Table 3). Results from studies with the panels of viruses having defined mutations in reverse transcriptase are listed in Tables 4 and 5. Mutations conferring resistance to ADAM II are clustered within the amino acid residues comprising the NNRTI binding pocket. Resistance mutations to the NNRTI $\alpha$-APA are located close to the bound inhibitor, and it therefore seems likely that the mutations conferring resistance to ADAM II may also be located close to the bound ligand. The mutations conferring greater than ten-fold resistance to ADAM II were located at positions 103, 108, 110, 139, 181, and 188. In contrast, the A98G and L1001 mutants were more sensitive to ADAM II than the corresponding wild type virus (Table 5). The virus containing the L100I mutation and the multiple mutations that confer resistance to AZT also displayed increased sensitivity to ADAM II. This suggests the possible clinical utility of ADAM II against AZT resistant strains of HIV-1 and against strains of HIV-1 that express L100I-based resistance to other NNRTIs.

TABLE 2

| Mechanistic Evaluations of ADAM II (22) | |
|---|---|
| Parameter | $IC_{50}$ ($\mu$M) |
| Attachment/Fusion | $NI_{100}$[a] |
| RT | |
| rAdT | 1.9 |
| rCdG | 0.3 |
| Integrase | $NI_{100}$[b] |
| Protease | >100[c] |
| Nucleocapsin p7 Protein | $NI_{25}$ |

[a] A 20% inhibition was observed at 100 $\mu$M.
[b] NI indicates that no inhibition of activity was observed at the indicated high test concentration.
[c] A 30% inhibition of HIV-1 protease was observed at a concentration of 100 $\mu$M.

TABLE 3

ADAM II Activity Against HIV-1 Laboratory-Adapted Strains, Lymphocyte-Tropic Clinical Isolates, Clades and Monocyte-tropic Strains of HIV-1

| Virus Isolate | Virus Type | Cell Type | $EC_{50}$ ($\mu M$) |
|---|---|---|---|
| HIV-1 RF | WT-Laboratory[a] | CEM-SS | 0.91 |
| HIV-1 IIIB | WT-Laboratory[a] | CEM-SS | 0.16 |
| HIV-1 TEKI | WT-Clinical[b] | PBMC | 2.20 |
| HIV-1 ROJO | WT-Clinical[b] | PBMC | 2.28 |
| HIV-1 | Clade A | PBMC | 1.09 |
| HIV-1 | Clade B | PBMC | 0.43 |
| HIV-1 | Clade C | PBMC | 1.04 |
| HIV-1 | Clade D | PBMC | 1.02 |
| HIV-1 | Clade E | PBMC | 0.40 |
| HIV-I | Clade F | PBMC | 1.70 |
| HIV-1 Ba-L | Monocyte-tropic | Mono/Mac | 0.36 |
| HIV-1 ADA | Monocyte-tropic | Mono/Mac | 0.28 |

[a]Wild type laboratory-adapted strain.
[b]Wild type clinical isolate.

TABLE 4

ADAM II Activity Against a Biological Panel of Resistant Isolates in CEM-CC Cells

| Virus Isolate | Mutation in RT | $EC_{50}$ ($\mu M$) | Fold Resistance |
|---|---|---|---|
| HIV-1 IIIB | Wild Type | 0.39 | |
| OC[a] | L100I | 0.94 | 2.4 |
| TSAO/Cost | K110E | 11.9 | 30 |
| 129/Cost | K103N | 10.8 | 28 |
| Thiazol[b] | V108I | >50 | >128 |
| Calo[c] | T139I | 15 | 38 |
| DPS[d] | Y181C | >50 | >128 |
| 3TC | M184I | 1.08 | 2.8 |
| Cost | Y188 H | >50 | >128 |
| HEPT[e] | P236L | 8.08 | 21 |

[a]Oxathiin carboxanilide resistant.
[b]Thiazolobenzimidazole resistant.
[c]Calanolide resistant.
[d]Diphenyl sulfonate resistant.
[e](Hydroxyethoxy)methyl(phenylthio)thymine resistant.

TABLE 5

ADAM II Activity Against a Site Directed Panel of Resistant Isolates in CEM-SS Cells

| Virus Isolate | Mutation in RT | $EC_{50}$ ($\mu M$) | Fold Resistance |
|---|---|---|---|
| HIV-1 NL4-3 | Wildtype | 1.78 | |
| | Y188C | 10.80 | 6.07 |
| | K103N | >50 | >28 |
| | K101E | 3.05 | 1.71 |
| | L100I | <0.16 | S[a] |
| | 4XAZT/L100I[b] | 0.27 | S[a] |
| | A98G | 0.84 | S[a] |
| | V179D | 50 | 28 |
| | Y181C | >50 | >28 |
| | L74V | 2.23 | 1.25 |
| | 4XAZT[b] | 0.90 | S[a] |
| | V108I | 12.0 | 6.74 |
| | V106A | 12.7 | 7.13 |
| | 4XAZT/Y181C[b] | >50 | >28 |

[a]Enhanced Sensitivity.
[b]AZT resistant.

EXAMPLE 3

Experimental Section

General. Melting points were determined in capillary tubes on a Mel-Temp apparatus and are uncorrected. Spectra were obtained as follows: CI mass spectra on a Finnegan 4000 spectrometer, FAB mass spectra and EI mass spectra on a Kratos MS50 spectrometer, $^1$H NMR spectra on Varian VXR-500S and Bruker ARX-300 spectrometers; IR spectra on a Beckman IR-33 spectrometer or on a Perkin Elmer 1600 series FTIR. Microanalyses were performed at the Purdue Microanalysis Laboratory, and all values were within ±0.4% of the calculated compositions.

3',3"-Dibromo-4',4"-dimethoxy-5',5"-bis (methoxycarbonyl)-1,1-diphenylethene (3). Methyl (triphenyl)phosphonium bromide (132 mg, 0.36 mmol) was suspended in anhydrous THF (2 mL), the mixture was stirred under Argon in an ice-bath, and sodium bis(trimethylsilyl)amide (1.0 M in THF, 0.4 mL, 0.4 mmol) was added by syringe. The mixture was stirred for 20 min, and a solution of 3,3'-dibromo-4,4'-dimethoxy-5,5'bis (methoxycarbonyl)diphenyl ketone (10) (155 mg, 0.3 mmol) in anhydrous THF (3 mL) was slowly injected. The ice bath was removed, and the reaction mixture was stirred for 1 h at ambient temperature and 1 h at 60° C. overnight at ambient temperature. The reaction was quenched with saturated ammonium chloride solution (3 mL). The yellow organic layer was separated and the aqueous layer was extracted with benzene (2×5 mL). The combined organic extracts were washed with brine (2 mL) and dried ($Na_2SO_4$). The solvent was evaporated and the residue was purified by flash chromatography on silica gel (6 g), eluting with hexane-ethyl acetate (6:1) to give 3 (62 mg 42%) as a colorless solid: mp 144–145° C.; $^1$H NMR (CDCl$_3$, 300 MHz) δ 7.70 (m, 2H), 7.68 (m, 2H), 5.53 (s, 2H), 4.01 (s, 3H), 4.00 (s, 3H), 3.97 (s, 3H), 3.96 (s, 3H); IR (KBr) 2943, 1730, 1472, 1434, 1246, 1208, 1086, 992, 797, 726 cm$^-$; CIMS m/z (rel intensity) 516 (27), 515 (96), 514 (21), 512 (M$^+$, 5), 486 (10), 485 (45), 484 (21), 483 (100). Anal. ($C_{20}H_{18}Br_2O_6 \cdot 1H_2O$) C, H.

3',3"-Dibromo-4',4"-dimethoxy-5',5"-bis (methoxycarbonyl)-1,1-diphenylpropene (4). Ethyl (triphenyl)phosphonium bromide (134 mg, 0.36 mmol) was suspended in anhydrous THF 2 mL, and the mixture was stirred under Ar in an ice-bath. Sodium bis(trimethylsilyl) amide (1.0 M in THF, 0.5 mL) was added by syringe. The mixture was stirred for 20 min, and a solution of 3,3'-dibromo-4,4'-dimethoxy-5,5'bis(methoxycarbonyl)diphenyl ketone (10) (155 mg, 0.3 mmol) in anhydrous THF (3 mL) was slowly injected. The ice-bath was removed, and the reaction mixture was stirred for 24 h at ambient temperature. The reaction was quenched with saturated ammonium chloride solution (3 mL). The yellow organic layer was separated and the aqueous layer was extracted with benzene (2×5 mL). The combined organic extracts were washed with brine (2 mL) and dried ($Na_2SO_4$). The solvent was evaporated and the residue purified by flash chromatography on silica gel (6 g), eluting with hexane-ethyl acetate (6:1), to afford 4 (55 mg, 35%) as a colorless solid: MP 76–77° C.; $^1$H NMR (CDCl$_3$, 300 MHz) δ 7.54 (m, 2H), 7.51 (m, 1H), 7.49 (m, 1H), 6.18 (q, J=7.2 Hz, 1H), 3.99 (s, 3H), 3.93 (s, 6H), 3.92 (s, 3H), 1.77 (d, J=7.2 Hz, 3H); IR (KBr) 2950, 1732, 1475, 1286, 1263, 1207, 997, 725 cm$^{-1}$; CIMS m/z (rel intensity) 531 (62), 530 (29), 529 (94), 528 (23), 527 (M+1, 57), 500 (12), 499 (53), 498 (24), 497 (100), 495 (53). Anal. ($C_{21}H_{20}OBr_2O_6$) C, H.

3',3"-Dibromo-4',4"-dimethoxy-5',5"-bis (methoxycarbonyl)-1-methoxy-2,2-diphenylethene (5). Methoxymethyl(triphenyl)phosphonium bromide (257 mg, 0.75 mmol) was suspended in anhydrous THF (4 mL), the mixture was stirred under Ar in an ice bath, and sodium bis(trimethylsilyl)amide (1.0 M in THF, 0.75 mL, 0.75 mmol) was added by syringe. The mixture was stirred for 20 min, and a solution of 3,3'-dibromo-4,4'-dimethoxy-5,5'bis(methoxycarbonyl)diphenyl ketone (10) (258 mg, 0.5 mmol) in anhydrous THF (4 mL) was slowly injected. The ice bath was removed, and the reaction mixture was stirred for 24 h at ambient temperature, 3 h at 60° C., and overnight at ambient temperature. The reaction was quenched with saturated ammonium chloride solution (5 mL). The yellow organic layer was separated and the aqueous layer was extracted with benzene (2×10 mL). The combined organic extracts were washed with brine (4 mL) and dried ($Na_2SO_4$). The solvent was evaporated and the residue purified by flash chromatography on silica gel (15 g), eluting with hexane-ethyl acetate 6:1, to give compound 5 as a colorless oil (76 mg, 28%) having an $R_f$ of 0.15 on silica gel when hexane-ethyl acetate (6:1) was used as the sovent system: $^1$H NMR ($CDCl_3$, 300 MHz) δ 7.78 (d, J=2.1 Hz, 1H), 7.74 (d, J=2.1 Hz, 1H), 7.61 (d, J=2.2 Hz, 1H), 7.58 (d, J=2.2 Hz, 1H), 6.51 (s, 1H), 4.01 (s, 6H), 3.99 (s, 3H), 3.97 (s, 3H), 3.89 (s, 3H); IR (neat) 2949, 1733, 1636, 1475, 1436, 1289, 1255, 1208, 1124, 1081, 1049, 998 $cm^{-1}$. HRFABMS calcd for $C_{21}H_{21}Br_2O_7$ m/z 542.9654. Found m/z 542.9661.

3',3"-Dibromo-4',4"-dimethoxy-5',5"-bis(methoxycarbony)-1,1-diphenyl-4-[(tert-butyldiphenylsilyl)oxy]-1-butene (6). 3-[tert-(Butyldiphenylsilyloxy)propyl] triphenylphosphonium bromide (595 mg, 0.93 mmol) was suspended in anhydrous THF (6 mL) and the mixture stirred under Ar on an ice bath. Sodium bis(trimethylsilyl)amide (1.0 M in THF, 1 mL) was added by syringe. The reaction mixture turned into a bright orange solution and was stirred in an ice bath for 30 min. A solution of the ketone 10 (320 mg, 0.62 mmol) dissolved in anhydrous THF (5 mL) was added and the reaction mixture was stirred at ambient temperature for 24 h. The mixture was quenched with saturated ammonium chloride solution (10 mL), followed by ethyl acetate (10 mL). The organic layer was separated and the aqueous layer was extracted with ethyl acetate (3×20 mL). The combined organic extracts were washed with brine (15 mL) and dried ($Na_2SO_4$). The solvent was evaporated and the yellow oily residue purified by flash chromatography on silica gel (20 g), eluting with hexane-ethyl acetate 3:1, to give 6 (284 mg, 58%) as a yellow oil: $^1$H NMR ($CDCl_3$, 300 MHz) δ 7.67 (d, J=7.7 Hz, 4H), 7.58 (m, 3H), 7.51 (d, J=2.1 Hz, 1H), 7.40 (m, 6H), 6.10 (t, J=7.4 Hz, 1H), 4.03 (s, 3H), 3.98 (s, 3H), 3.95 (s, 3H), 3.93 (s, 3H) 3.79 (t, J=6.1 Hz, 2H), 2.39 (m, 2H), 1.09 (s, 9H); IR (neat) 2951, 2860, 1734, 1473, 1265, 1205, 998, 704 $cm^{-1}$. Anal. ($C_{38}H_{40}Br_2O_7Si$) C, H.

3',3"-Dibromo-4-hydroxy-4',4"dimethoxy-5',5"-bis(methoxycarbony)-1,1-diphenyl-1-butene (7). Compound 6 (266 mg, 0.33 mmol) was dissolved in dry THF (7 mL) and the solution stirred at 0° C. under Ar. A 1.0 M solution of tetrabutylammonium fluoride in THF (0.7 mL, 0.7 mmol) was added. The solution turned yellow and was stirred at 0° C. for 5.5 h. Brine (10 mL) was added and the phases were separated. The aqueous phase was extracted with ethyl acetate (3×20 mL). The extract was dried ($MgSO_4$) and the solvent was evaporated. The residue was purified by flash column chromatography on silica gel, eluting with hexane-ethyl acetate 3:1, 1:1 to give 7 (129 mg, 70%) as a yellowish oil: $^1$H NMR ($CDCl_3$, 300 MHz) δ 7.58 (m, 3H), 7.52 (m, 1H), 6.14 (t, J=7.1 Hz, 1H), 4.00 (s, 3H), 3.96 (s, 3H), 3.94 (s, 3H), 3.93 (s, 3H), 3.77 (t, J=6.1 Hz, 2H), 2.41 (q, J=6.3 Hz, 2H), 1.59 (brs, 1H); IR (neat) 3430 (broad band), 2951, 1732, 1474, 1265, 1208, 998 $cm^{-1}$. Anal. ($C_{22}H_{22}Br_2O_7$) C, H.

3',3"-Dibromo-4-methanesulfonyloxy-4',4"dimethoxy-5',5"-bis(methoxycarbony)-1,1-diphenyl-1-butene (8). Compound (7) (310 mg, 0.55 mmol) and anhydrous triethylamine (0.23 mL, 1.7 mmol) were dissolved in dry dichloromethane (7 mL) and the mixture was stirred under Ar at 0° C. Mesyl chloride (0.2 mL, 2.56 mmol) was added and the mixture was stirred at 0° C. for 3 h. The reaction mixture was diluted with dichloromethane (10 mL) and washed with 0.5 N HCl (2×20 mL, followed by sat $NaHCO_3$ (1×20 mL) and brine (1×20 mL). The organic extract was dried ($MgSO_4$). The solvent was evaporated and the residue purified on silica gel (16 g), eluting with hexane-ethyl acetate 3:1, to afford the mesylate 8 (270 mg, 77%) as a colorless oil: $^1$H NMR ($CDCl_3$, 300 MHz) δ 7.55 (m, 2H), 7.51 (m, 2H), 6.14 (t, J=7.4 Hz, 1H), 4.30 (t, J=6.2 Hz, 2H), 3.99 (s, 3H), 3.931 (s, 3H), 3.927 (s, 3H), 3.92 (s, 3H), 3.04 (s, 3H), 2.56 (q, J=7.0 Hz, 2H); IR (neat) 2952, 1732, 1474, 1358, 1265, 1175, 1089, 995 $cm^{-1}$. Anal. ($C_{23}H_{24}Br_2SO_9$) C, H.

4-Azido-3',3"-Dibromo-4',4"dimethoxy-5',5"-bis(methoxycarbony)-1,1-diphenyl-1-butene (9). Compound 8 (231 mg, 0.363 mmol) was dissolved in dry N,N-dimethylformamide (5 mL). Sodium azide (120 mg, 1.82 mmol) was added and the mixture was stirred at 35–50° C. for 3 h. The reaction mixture was allowed to reach ambient temperature and then it was diluted with ethyl ether (42 mL). The ethereal solution was washed with water (2×35 mL), brine (1×35 mL), and dried ($MgSO_4$). The solvent was evaporated and the residue was purified on silica gel (16 g), eluting with hexane-ethyl acetate 3:1, to give 9 (132 mg, 62%) as a colorless solid: mp 69–70° C.; $^1$H NMR ($CDCl_3$, 300 MHz) δ 7.56 (m, 3H), 7.50 (m, 1H), 6.05 (m, 1H), 3.99 (m, 1H), 3.93 (m, 3H), 3.40 (m, 2H), 2.41 (m, 2H); IR (KBr) 2944, 2105, 1731, 1473, 1436, 1246, 1207, 1085, 999, 806, 726 $cm^1$. Anal ($C_{22}H_{21}Br_2N_3O_6$) C, H.

3',3"-Dibromo-4',4"-dimethoxy-5',5"-bis(methoxycarbonyl)-1,1,-diphenyl-1-heptene Epoxide (12). Compound 1 (67 mg, 0.116 mmol) was dissolved in dry methylene chloride (1 mL) and the solution cooled in a freezer for 5 min. 3-Chloroperoxybenzoic acid [minimum 57% (70 mg)] was dissolved in $CH_2Cl_2$ (0.5 mL and injected into the solution. The mixture was allowed to reach ambient temperature and was stirred for 21 h. Solvent was evaporated and the residue was purified by flash column chromatography on silica gel (7.5 g), eluting with hexane-ethyl acetate 20:1 followed by 10:1, to give the epoxide 12 (43 mg, 62%) as an oil: $^1$H NMR ($CDCl_3$, 300 MHz) δ 7.74 (m, 2H), 7.67 (m, 1H), 7.65 (m, 1H), 3.97 (s, 3H), 3.94 (s, 3H), 3.93 (s, 3H), 3.92 (s, 3H), 3.35 (m, 1H), 1.45 (m, 4H) 1.27 (m, 5H), 0.88 (m, 3H), IR (neat) 2953, 1732, 1472, 1435, 1260, 1207, 1087, 999, 720 $cm^{-1}$. Anal. ($C_{25}H_{28}Br_2O_7$) C, H.

2-(Trimethylsilyl)ethyl 3',3"-Dichloro-4',4"-dimethoxy-5,5"-bis(methoxycarbonyl)-3,3-diphenylpropenoate (13). A suspension of sodium hydride (0.018 g, 0.750 mmol) in dry THF (5 mL) was stirred in an ice bath under an argon atmosphere. Phosphonoacetate 24 (0.21 mL, 0.70 mmol) was added and the mixture was stirred at 0° C. for 1 h. The initial suspension turned into a clear solution within minutes. A solution of ketone 11 (0.200 g, 0.469 mmol) in dry THF (4 mL) was then added dropwise. The ice bath was removed and the reaction mixture was stirred at rt for 30 h. The solvent was removed and the residue was taken up in cold water (30 mL) and ethyl ether (30 mL). The layers were separated and the aqueous one was extracted with ethyl ether (2×30 mL). The combined organic fractions were washed with brine (2×30 mL), dried over magnesium sulfate and filtered. The solvent was removed in vacuo to give a residue. After flash chromatography ($SiO_2$, 35 g; column dimensions: 3 cm×6.5 inch), eluting with hexanes:ethyl acetate 5:1, compound 13 (0.216 g, 81.2%) was obtained as a thick oil: $^1$H NMR (300 MHz, CDCl$_3$) δ 7.60 (d, J=2.4 Hz, 1H), 7.53 (d, J=2.2 Hz, 1H), 7.39 (d, J=3.1 Hz, 1H), 7.38 (d, J=2.5 Hz, 1H), 6.31 (s, 1H), 4.11 (m, J=8.7 Hz, 2H), 3.99 (s, 3H), 3.95 (s, 3H), 3.91 (s, 3H), 3.90 (s, 3H), 0.89 (m, J=8.7 Hz, 2H), 0.01 (s, 9H); IR (film) 2952, 1737, 1477, 1251, 1161, 997, 859, 744 cm$^{-1}$; FABMS (m/z): 568.8 [MH]$^+$. Anal. (C$_{26}$H$_{30}$Cl$_2$O$_8$Si) C, H.

3',3"-Dichloro-4',4"-dimethoxy-5',5"-bis(methoxycarbonyl)-3,3-diphenylpropenoic Acid (14). A solution of ester 13 (0.198 g, 0.348 mmol) in dry THF (10 mL) was stirred under argon in an ice bath. A 1.0 M solution of TBAF (0.7 mL, 0.697 mmol) was added dropwise and the reaction mixture stirred at 0° C. for 1.5 h. The mixture turned into a light yellowish solution. Brine (30 mL) was added and the mixture stirred for 10 min. A 1.0 N solution of HCl (10 mL) was then added and the product was extracted with ethyl ether (3×30 mL). The combined organic extracts were washed with brine (1×40 mL), dried over magnesium sulfate, filtered, and the solvent removed. Pure 14 (0.135 g, 83%) was obtained as a colorless crystalline solid after flash chromatography (SiO$_2$, 20 g; column dimensions: 2.2 cm×6.5 inch), using chloroform:methanol:formic acid (200:10:0.1 mL) as eluant: mp. 60–62° C.; IR (film) 3400–2900, 2955, 1731, 1477, 1262, 1210, 1164, 994, 743 cm$^-$; $^1$H NMR (300 NIHz, CDCl$_3$) δ 7.59 (d, J=2.4 Hz, 1H), 7.50 (d, J=2.2 Hz, 1H), 7.37 (d, J=2.2 Hz, 1H), 7.35 (d, J=2.4 Hz, 1H), 6.29 (s, 1H), 3.97 (s, 3H), 3.93 (s, 3H), 3.89 (s, 3H), 3.88 (s, 3H); CIMS (m/z): 469 [MH, 25]$^+$, 451 [MH-18, 100]$^+$, 437 [MH-32, 23]$^+$. Anal. (C$_{21}$H$_{18}$Cl$_2$O$_8$0.4H$_2$O) C, H.

Methyl 3',3"-Dichloro-4',4"-dimethoxy-5,5Δ-bis(methoxycarbonyl)-3,3-diphenylpropenoate (15). A suspension of sodium hydride (0.012 g, 0.493 mmol) in dry THF (5 mL) was stirred in an ice bath under an argon atmosphere. Methyl diethylphosphonoacetate (27) (0.09 m.L, 0.469 mmol) was added and the mixture was stirred at 0° C. for 1 h. The initial suspension turned into a clear solution within minutes. A solution of ketone 11 (0.100 g, 0.235 mmol) in dry THF (5 mL) was added dropwise. The ice bath was removed and the reaction mixture was stirred at rt for 30 h. Cold water (15 mL) was added and the mixture was stirred for 10 min. The product was extracted with ethyl ether (3×25 mL). The combined organic fractions were washed with brine (1×30 mL), dried over magnesium sulfate, and filtered. The solvent was removed in vacuo to give a residue. After purification by flash chromatography on silica gel (35 g; column dimensions: 2 cm×6 inch), eluting with hexanes-:ethyl acetate 2:1, compound 15 (0.0948 g, 83.8%) was obtained as a thick colorless oil: $^1$H NMR (300 MHz, CDCl$_3$) δ 7.59 (d, J=2.4 Hz, 1H), 7.53 (d, J=2.2 Hz, 1H), 7.37 (d, J=2.2 Hz, 1H), 7.36 (d, J=2.4 Hz, 1H), 6.32 (s, 1H), 3.99 (s, 3H), 3.94 (s, 3H), 3.89 (s, 3H), 3.88 (s, 3H), 3.63 (s, 3H); IR (film) 2951, 1731, 1477, 1435, 1264, 1164, 996 cm$^-$; CIMS (m/z): 483 [MH, 30]$^+$ and 451 [(MH)$^+$–CH$_3$OH, 100]. Anal. (C$_{22}$H$_{20}$Cl$_2$O$_8$) C, H.

tert-Butyl 3',3"-Dichloro-4',4"-dimethoxy-5,5"-bis(methoxycarbonyl)3,3-diphenylpropenoate (16). tert-Butyl diethylphosphonoacetate (28) (0.44 mL, 1.872 mmol) was dissolved in dry THF (15 mL) and the mixture was stirred under argon in an ice bath. A 1.0 M solution of sodium bis(trimethylsilyl)amide (2.0 mL, 2.01 mmol) was added and the solution was stirred at 0° C. for 1 h. At this time, a solution of the ketone 11$^{34}$ (0.400 g, 0.936 mmol) in dry THF (12 mL) was added dropwise and the resulting mixture was stirred at rt for 24 h. The solvent was evaporated and the residue partitioned between ethyl ether (40 mL and water (60 mL). The layers were separated and the aqueous one was extracted with ethyl ether (2×40 mL). The combined organic extracts were dried over magnesium sulfate, filtered, and the solvent removed in vacuo to give a yellowish oil. Purification by flash chromatography (SiO$_2$, 30 g), eluting with hexanes-ethyl acetate (3:1), afforded pure 10 (0.229 g, 46.6%) as a white solid: mp 114–115.5° C.; $^1$H-NMR (300 MHz, CDCl$_3$) δ 7.57 (d, J=2.4 Hz, 1H), 7.51 (d, J=2.3 Hz, 1H), 7.37 (d, J=2.2 Hz, 1H), 7.35 (d, J=2.4 Hz, 1H), 6.22 (s, 3H), 3.98 (s, 3H), 3.94 (s, 3H), 3.90 (s, 3H), 3.88 (s, 3H), 1.29 (s, 3H); IR (film) 2952, 1731, 1479, 1368, 1258, 1095, 998, 848, 744 cm$^{-1}$; CIMS m/z (relative intensity) 451 (MH$^+$–C$_4$H$_8$, 100), 469 (MH$^+$–C$_4$H$_9$OH, 92), 470 (MH$^+$–C$_4$H$_9$O, 64). Anal. (C$_{25}$H$_{26}$Cl$_2$O$_8$,) C, H.

3',3"-Dichloro-4',4"-dimethoxy-5',5"-bis(methoxycarbony)-1,1-diphenyl-4-[(tert-butyldiphenylsilyl)oxy]-1-butene (17). 3-[tert-(Butyldiphenylsilyloxy)propyl]triphenylphosphonium bromide (0.45 g, 0.702 mmol) was suspended in dry THF (5 mL) and stirred under argon. The suspension was cooled in an ice bath. A 1.0 M solution of NaHMDS (0.75 mL, 0.75 mmol) in THF was added dropwise. The reaction mixture turned into a bright orange solution and was stirred in the ice bath for 30 min. A solution of the ketone 11 (0.200 g, 0.468 mmol) in dry THF (2 mL) was added. The solution was stirred at room temperature for 24 h. A saturated solution of ammonium chloride (10 mL was then added, followed by ethyl acetate (10 mL). The phases were separated and the aqueous one was extracted with ethyl acetate (3×20 mL). The combined organic extracts were washed with brine (1×40 mL), dried over magnesium sulfate, filtered, and the solvent evaporated to give a dark brown oil. Purification by flash chromatography (SiO$_2$), eluting with hexane/ethyl acetate (3:1), provided 17 (0.26 g, 76%) as a yellowish oil: $^1$H-NMR (300 MHz, CDCl$_3$) δ 7.63 (dd, J=1.4 Hz, 4H), 7.49 (d, J=2.3 Hz, 1H), 7.46 (d, J=2.1 Hz, 1H), 7.31 (d, J=2.0 Hz, 1H), 7.28 (d, J=2.3 Hz, 1H), 7.34 (m, 6H), 6.10 (t, J=7.4 Hz, 1H), 3.99 (s, 3H), 3.94 (s, 3H), 3.90 (s, 3H), 3.88 (s, H), 3.75 (t, J=6.1 Hz, 2H), 2.36 (t, J=6.3 Hz, 1H), 2.34 (t, J=6.4 Hz, 1H), 1.05 (s, 9H); IR (film) 3050, 2951, 1737, 1475, 1428, 1270, 1202, 1093, 999, 910, 702 cm$^{-1}$. Anal. (C$_{38}$H$_{40}$Cl$_2$O$_7$Si) C, H.

3',3"-Dichloro-4-hydroxy-4',4"dimethoxy-5',5"-bis(methoxycarbony)-1,1-diphenyl-1-butene (18). Silyl ether 17 (0.2 g, 0.282 mmol) was dissolved in dry THF (6 mL) and stirred at 0° C. under argon. A 1.0 M solution of tetrabutylammonium fluoride in THF (0.6 mL, 0.6 mmol) was added and the initially yellow solution turned into an orange solution which was stirred at 0° C. for 5.5 h. Brine (10 mL) was added and the phases were separated. The aqueous one was extracted with ethyl acetate (3×20 mL). The combined organic extracts were washed with brine (1×40 mL), dried over magnesium sulfate, filtered and the solvent evaporated to give an orange oil. Purification by flash chromatography (silica gel) using hexane/ethyl acetate 1:1 as the eluant afforded 18 (94.5 mg, 71.4%) as a colorless oil: $^1$H NMR (300 MHz, CDCl$_3$) δ 7.52 (d, J=2.4 Hz, 1H), 7.50 (d, J=2.1 Hz, 1H), 7.37 (d, J=2.1 Hz, 1H), 7.31 (d, J=1.8 Hz, 1H), 6.13 (t, J=7.4 Hz, 1H), 3.99 (s, 3H), 3.93 (s, 3H), 3.92 (s, 3H), 3.91 (s, 3H), 3.75 (t, J=6.3 Hz, 2H), 2.38 (q, J=13.4 and J=6.7 Hz, 1H), 1.66 (bs, 1H); IR (film) 3542, 2951, 2874, 1732, 1477, 1428, 1268, 1210, 1093, 998, 866, 743 cm$^{-1}$.

3',3"-Dichloro-4',4"-dimethoxy-5',5"-bis(carboxy)-4,4-diphenyl-3-butenoic Acid (23). Chromium trioxide (0.64 g, 6.39 mmol) was dissolved in 1.5 M sulfuric acid (9.3 mL, 13.9 mmol), and the solution was stirred in an ice bath. A solution of alcohol 18 (0.50, 1.065 mmol) in acetone (15 mL) was then added and the ice bath removed. The reaction mixture was stirred at room temperature for 7 h. Ethyl ether (50 mL) was added and the phases separated. The organic phase was washed with water (3×40 mL) and then extracted with 3 M sodium hydroxide (3×20 mL). The combined aqueous extracts were acidified with conc hydrochloric acid and the cloudy solution was kept in the refrigerator overnight. Separation of the precipitated solid by filtration, followed by washing with water, afforded a yellowish solid (0.131 g), which was purified by recrystallization from ethyl ether/dichloromethane to yield 19 (63 mg, 12.2%) as a pale yellow solid: mp 206–207° C.; $^1$H NMR (300 MHz, acetone-$d_6$) δ 7.65 (d, J=2.3 Hz, 1H), 7.62 (d, J=2.1 Hz, 1H), 7.57 (d, J=2.1 Hz, 1H), 7.52 (d, J=2.3 Hz, 1H), 6.42 (t, J=7.4 Hz, 1H), 3.97 (s, 6H), 3.91 (s, 6H), 3.20 (d, J=7.4 Hz, 2H); IR (film) 3400–2800, 2938, 1702, 1478, 1259, 996, 708 cm$^{-1}$; FABMS m/z (rel intesity): 454 (M$^+$, 45), 437 (M$^+$−17, 100). Anal. ($C_{20}H_{16}Cl_2O_8$·0.4$H_2O$) C, H.

3',3"-Dichloro-4-methanesulfonyloxy-4',4"dimethoxy-5', 5'-bis(methoxycarbony)-1,1-diphenyl-1-butene (19). A solution of alcohol 18 (0.700 g, 1.491 mmol) and triethylamine (0.62 mL, 4.473 mmol) in dry dichloromethane (20 mL was stirred under argon at 0° C. Mesyl chloride (0.35 mL, 4.473 mmol) was added and the mixture was stirred at 0° C. for 3 h. The reaction mixture was then diluted with dichloromethane (30 mL) and washed with 0.5 N HCl (2×40 mL), followed by sat NaHCO$_3$ (40 mL) and brine (40 mL). The organic extract was dried over magnesium sulfate, filtered, and the solvent removed in vacuo to produce a thick yellow oil (0.77 g). Purification of a fraction of this oil (0.557 g) by flash chromatography (25 g SiO$_2$) afforded pure 19 (0.521 g, 88.5%) as a thick oil, which slowly crystallized. The analytical sample was obtained by recrystallization from chloroform-methanol: mp. 83–85° C.; IR (film) 2952, 1731, 1479, 1359, 1269, 1174, 995 cm$^{-1}$; $^1$H-NMR (300 MHz, CDCl$_3$) δ 7.49 (d, J=2.4 Hz, 1H), 7.47 (d, J=2.2 Hz, 1H), 7.31 (d, J=2.1 Hz, 1H), 7.29 (d, J=2.3 Hz, 1H), 6.04 (t, J=7.4 Hz, 1H), 4.27 (t, J=6.3 Hz, 2H), 3.97 (s, 3H), 3.91 (s, 3H), 3.89 (s, 3H), 3.88 (s, 3H), 3.00 (s, 3H), 2.53 (q, J=6.4 Hz and J=7.2 Hz, 2H); CIMS m/z (relative intensity) 547 (MH$^+$, 46), 515 (100). Anal. ($C_{23}H_{24}Cl_2O_9S$) C, H.

4-Azido-3',3"-Dichloro-4',4"dimethoxy-5',5'-bis(methoxycarbony)-1,1-diphenyl-1-butene (20). Mesylate 19 (0.215 g, 0.393 mmol) was dissolved in dry DMF (5 mL). Sodium azide (0.13 g, 1.965 mmol) was added and the mixture was stirred at 35 to 50° C. for 3 h. The mixture was allowed to cool at room temperature, and then it was diluted with ether (45 mL). The ethereal solution was washed with water (2×40 mL), brine (1×40 mL), and dried over magnesium sulfate. After filtration and evaporation of the solvent in vacuo, a yellowish oil was obtained. Purification by flash chromatography (SiO$_2$, 16 g), eluting with hexane:ethyl acetate 3:1, afforded pure 20 (0.148 g, 76.1%) as an oil which slowly crystallized. The analytical sample was obtained by recrystallization from chloroform-pentane: mp 70–72° C.; $^1$H NMR (300 MHz, CDCl$_3$) δ 7.50 (t, J=2.1 Hz, 2H), 7.34 (d, J=2.2 Hz, 1H), 7.30 (d, J=2.4 Hz, 1H), 6.05 (t, J=7.4 Hz, 1H), 3.99 (s, 3H), 3.92 (s, 3H), 3.91 (s, 3H), 3.90 (s, 3H), 3.39 (t, J=6.6 Hz, 2H), 2.39 (q, J=6.7 Hz and J=7.2 Hz, 2H); IR (film) 2952, 2098, 1734, 1477, 1267, 997, 742 cm$^{-1}$; CIMS m/z (relative intensity) 494 (MH$^+$, 100), 496 (70). Anal. ($C_{22}H_{21}Cl_2N_3O_6$·0.5$H_2O$) C, H.

4-Amino-3',3"-Dichloro-4',4"dimethoxy-5',5"-bis(methoxycarbony)-1,1-diphenyl-1-butene (21). A solution of azide 20 (0.228 g, 0.462 mmol) and (EtO)$_3$P (0.24 mL, 1.387 mmol) in benzene (6 mL) was stirred under argon at rt for 24 h. The reaction mixture was then saturated with dry HCl for 10 min and stirred for 48 h at rt. The solvent was removed and dry ethyl ether (15 mL) was added. The solution was placed in the freezer for 48 h. The precipitated amine hydrochloride was separated by filtration, washed with cold ethyl ether, and dried under high vacuum overnight to provide 21 (0.200 g, 86%) as a white solid. The analytical sample was recrystallized from ethanol-ethyl ether-pentane: mp 156–158° C.; $^1$H NMR (300 MHz, CDCl$_3$) δ 7.49 (t, J=2.3 Hz, 2H), 7.47 (d, J=2.2 Hz, 1H), 7.32 (d, J=2.2 Hz, 1H), 7.29 (d, J=2.4 Hz, 1H), 6.06 (t, J=7.4 Hz, 1H), 3.96 (s, 3H), 3.90 (s, 3H), 3.89 (s, 3H), 3.88 (s, 3H), 2.81 (t, J=6.6 H$_2$, 2H), 2.25 (q, J=7.1 Hz, 2H), 1.90 (bs, 2H), exchangeable with D$_2$O; IR (film) 2951, 1731, 1476, 1435, 1261, 1208, 997, 742 cm$^{-1}$; CIMS m/z (rel intesity) 467 (M$^+$, 90), 466 (M$^+$−1, 100). Anal. ($C_{22}H_{23}Cl_2NO_6$·HCl) C, H, N.

Methyl 3',3"-Dichloro-4',4"-dimethoxy-5,5"-bis(methoxycarbonyl)-6,6-diphenylhexenoate (22). (4-Methoxycarbonylbutyl)triphenylphosphonium bromide (29) (0.321 g, 0.704 mmol) was stirred in dry THF (15 mL) under argon at −78° C. A 1.0 M solution of NaN(SiMe$_3$)$_2$ in THF (0.78 mL, 0.78 mmol) was then added and the yellow solution was stirred in a dry ice-acetone bath for 1 h. A −78° C. solution of ketone 11 (0.200 g, 0.469 mmol) in dry THF (5 mL) was added and the reaction mixture was stirred at −78° C. for 12 h, and then at rt for 12 h. Saturated NH$_4$Cl (25 mL) was added and the mixture stirred for 15 min. The layers were separated and the aqueous phase was extracted with ethyl acetate (3×30 mL). The combined organic extracts were washed with brine (1×40 mL), dried over magnesium sulfate, filtered, and the solvent removed in vacuo to give a thick orange residue. Purification was achieved by silica gel flash chromatography, eluting with hexane:ethyl acetate 3:1, to provide 22 (0.110 g, 44.6%) as a pale yellow oil: $^1$H NMR (300 MHz, CDCl$_3$) δ 7.51 (d, J=2.3 Hz, 1H), 7.48 (d, J=2.2 Hz, 1H), 7.33 (d, J=2.2 Hz, 1H), 7.30 (d, J=2.3 Hz, 1H), 6.05 (t, J=7.5 Hz, 1H), 4.01 (s, 3H), 3.95 (s, 3H), 3.94 (s, 3H), 3.93 (s, 3H), 3.65 (s, 3H), 2.32 (t, J=7.4 Hz, 2H), 2.15 (q, J=7.4 Hz, 2H), 1.80 (m, J=7.3 Hz, 2H); IR (film) 2951, 1736, 1477, 1261, 1208, 1093, 999, 743 cm$^{-1}$; FABMS m/z: (rel intensity) 525 (MH$^+$, 30), 509 (M$^+$−CH$_3$, 28), 493 (M$^+$−OCH$_3$, 100). Anal. ($C_{25}H_{26}Cl_2O_8$) C, H.

Following a similar procedure using 4-carboxybutyltriphenyl phosphonium bromide instead of 29 above, provided the corresponding 6,6-diphenyl hexanoic acid. (2-Trimethylsilyl)ethyl Diethylphosphonoacetate (24). BOP-Cl (2.53 g, 9.952 mmol) was added to a solution of diethylphosphonoacetic acid (25) (1.6 mL, 9.952 mmol), (2-trimethylsilyl)ethanol (26) (1.57 mL, 10.94 mmol), and triethylamine (2.77 mL, 19.904 mmol) in dry dichloromethane (25 mL). The initial suspension turned into a clear solution within minutes, which was stirred at rt under Ar for 1.2 h. Water (60 mL, basified with sodium bicarbonate) was added and the phases were separated. The organic phase was diluted with dichloromethane (2×30 mL) and washed with water (1×50 mL and brine (1×50 mL). The organic phase was dried over magnesium sulfate, filtered and the solvent removed in vacuo to give a liquid residue (6.89 g). Purification by flash chromatography (SiO$_2$, 135 g) afforded 24 as a colorless liquid (2.47 g, 84%): bp 120–122° C./0.05 mm Hg (Lit.[38] 140–145° C./0.1 mm Hg); IR (film) 2981, 2954, 2904, 1737, 1268, 1027, 969, 838 cm$^{-1}$; $^1$H NMR (300 MHz, CDCl$_3$) δ 4.18 (m, J=8.6 Hz, 2H), 4.14 (m, J=7.2 Hz, 4H), 2.94 (s, 1H), 2.87 (s, 1H), 1.31 (t, J=7.1 Hz, 6H), 0.98 (m, J=8.7 Hz, 2H), 0.01 (s, 9H). Anal ($C_{11}H_{25}O_5PSi$) C, H.

1-Bromo-4,4-bis(8',8"-dichloro-2',2',2",2"-tetramethyl-4', 4"-dioxo-6',6"-0(1,3-benzodioxyl)]-3-butene (31). A solution of the alcohol 31 (0.106 g, 0.215 mmol) and carbon tetrabromide (0.09 g, 0.271 mmol) in dry acetonitrile (8.5 mL) was stirred under argon. A solution of triphenylphosphine (0.08 g, 0.305 mmol) in dry acetonitrile (1.5 mL) was added dropwise. The reaction mixture was stirred at reflux for 20 h. The solvent was removed in vacuo and the resulting oil was extracted with ethyl ether (5×5 mL). The solvent was evaporated from the combined organic extracts to give a thick solid. Purification by flash chromatography ($SiO_2$, 25 g), eluting with hexane-ethyl acetate 5:1, afforded the product 31 (66 mg, 56%) as a yellowish solid: mp 175–178° C.; $^1$H NMR ($CDCl_3$, 300 MHz) δ 7.70 (d, J=2.0 Hz, 1H), 7.69 (d, J=1.8 Hz, 1H), 7.45 (d, J=2.2 Hz, 1H), 7.44 (d, J=2.1 Hz, 1H), 6.09 (t, J=7.2 Hz, 1H), 3.45 (t, J=6.5 Hz, 2H), 2.70 (q, J=6.7 Hz, 2H), 1.84 (s, 6H), 1.80 (s, 6H); IR (film) 2999, 1745, 1607, 1483, 1283, 1199, 1063, 874, 756 $cm^{-1}$; CIMS m/z (rel intensity) 555 ($MH^+$, 55), 557 ($MH^+$+2, 100), 559 ($MH^+$+4, 40). Anal. ($C_{24}H_{21}BrCl_2O_6$) C, H.

4,4'-Dimethoxy-3,3'-bis(methoxycarbonyl) diphenylmethane (34). A suspension of 3,3'-dicarboxy-4,4'-dihydroxydiphenylmethane (33) (0.576 g, 2 mmol), dimethylsulfate (2 mL, 12 mmol), and potassium carbonate (2.0 g) in acetone (20 mL) was heated at reflux for 6 h. The solid mass was separated by filtration and washed with acetone. Evaporation of the acetone gave the product 34 (0.51 g, 80%) as a brown oil: $^1$H NMR ($CDCl_3$, 300 MHz) δ 7.61 (d, J=1.8 Hz, 2H), 7.25 (dd, J=1.8, 8.6 Hz, 2H), 6.90 (d, J=8.5 Hz, 2H), 3.90 (s, 2H), 3.87 (s, 6H). Anal. ($C_{19}H_{20}O_6$) C, H.

4,4'-Dimethoxy-3,3'-bis(methoxycarbonyl)benzophenone (35). A solution of intermediate 34 (0.5 g, 1.8 mmol) in acetic anhydride (25 mL) was cooled to 0° C. in an ice bath containing NaCl. Solid chromium (VI) oxide (3 g, 30 mmol) was added slowly to the solution at 0° C. After complete addition, the mixture was stirred at 0° C. for 1 h, and then room temperature for 12 h. The resulting viscous paste was broken up with ethyl acetate and partitioned between 1 N HCl (200 mL) and ethyl acetate (200 mL). The organic layer was washed with 1 N HCl (100 mL) and brine (100 mL), dried over $Na_2SO_4$, and the solvent removed under reduced pressure. Trituration of the solid in 1 N HCl and filtering gave the product 35 (0.12 g, 22%) as an off white solid: mp 142–144° C.; $^1$H NMR (acetone-$d_6$) 8.14 (d, J=2.2 Hz, 2H), 7.96 (dd, J=2.2, 8.7 Hz, 1H), 7.30 (d, J=8.7 Hz, 1H), 3.99 (s, 3H), 3.84 (s, 3H). FTIR (KBr) 2953, 2849, 1735, 1710, 1650, 1603, 1502, 1438, 1406, 1274, 1152, 1081, 1010, 950 $cm^{-1}$. Anal. ($C_{19}H_{18}O_7$) C, H.

4',4"-Dimethoxy-3',3"-bis(methoxycarbonyl)-1,1-diphenyl-1-heptene (36). n-Hexyltriphenylphosphonium bromide (0.427 g, 1 mmol) was dried by azeotropic distillation from a benzene solution and then stirred in dry THF (10 mL) under nitrogen atmosphere. Sodium bis (trimethylsilyl)amide (1 M in THF, 1 mL, 1 mmol) was added and the ylide produced was stirred under nitrogen at 0° C. for 30 min. Intermediate 35 (0.276 g, 0.77 mmol) was added as a solution in THF (10 mL) under nitrogen. The mixture was stirred at rt overnight and partitioned between 1 N HCl (100 mL) and ethyl acetate (100 mL). The organic layer was dried over sodium sulfate, and evaporated to afford an oil which was chromatographed on $SiO_2$ (230–400 mesh, 50 g), eluting with hexanes/ethyl acetate (4:1) to give the product (36) (0.15 g, 46%) as an oil: $^1$H NMR ($CDCl_3$, 300 MHz) δ 7.63 (d, J=2.3 Hz, 1H), 7.56 (d, J=2.2 Hz, 1H), 7.20 (dt, J=2.3 Hz, 1H), 6.94 (d, J=8.6 Hz, 1H), 6.82 (d, J=8.7H, 1H), 5.96 (t, J=7.5 Hz, 1H), 3.90 (s, 3H), 3.84 (s, 3H), 3.83 (s, 6H), 2.05 (q, J=7.3 Hz, 2H), 1.39 (t, J=7.2 Hz, 2H), 1.22 (m, J=1.9 Hz, 2H), 0.83 (t, J=6.7 Hz, 3H); IR (neat) 2927, 2853, 1732, 1606, 1500, 1435, 1263 $cm^{-1}$. Anal. ($C_{25}H_{30}O_6$) C, H.

4,4'-Dimethoxy-3,3'-bis(methoxycarbonyl)-5,5'-dinitrobenzophenone (37). A solution of compound 36 (1.07 g, 3 mmol) in acetic anhydride (30 mL) was cooled to 0° C. Nitric acid 90%, 20 mL was added dropwise and the solution was stirred overnight while warming to room temperature. The orange solution was poured onto ice and water and extracted with ethyl acetate (3×100 mL). The organic layer was washed with 5% KOH solution (3×50 mL), dried over $MgSO_4$, and evaporated. The oil (1.1 g) was flash chromatographed on silica gel (250 g, 230–400 mesh), eluting with hexanes-ethyl acetate (10:2), to afford 37 (0.41 g, 32%) as a solid: mp 96–98° C.; $^1$H NMR ($CDCl_3$, 300 MHz) 58.55 (s, 2H), 8.41 (s, 2H), 4.1 (s, 6H), 3.99 (s, 6H). Anal. ($C_{19}H_{16}H_2O_7$) C, H, N.

3,3'-Diamino-5,5'-Bis(methoxycarbonyl)-4 4'-dinitroxybenzophenone (38). The dinitro compound 37 (0.33 g, 0.9 mmol) was hydrogenated at atmospheric pressure over platinum oxide (0.2 g, 0.08 mmol) in ethyl acetate (50 mL). After tlc ($SiO_2$, hexanes-acetone, 10:2) had shown that all the starting material was consumed, the catalyst was removed by filtration and the solvent was removed at reduced pressure to give an oil. This oil was flash chromatographed on $SiO_2$ (30 g, 230–400 mesh) using ethyl acetate. Evaporation of the solvent gave the product 38 (0.24 g, 80%) as a glassy solid; $^1$H NMR ($CDCl_3$, 300 MHz) δ 7.55 (d, J=2.1 Hz, 2H), 7.31 (d, J=2.1 Hz, 2H), 3.91 (s, 6H), 3.89 (s, 6H); IR (KBr) 3369, 2945, 2837, 1717, 1616 $cm^{-1}$. Anal. ($C_{19}H_{20}N_2O_7$)

3,3'-Diiodo-4,4',-dimethoxy-5,5'-bis(methoxycarbonyl) benzophenone (39). A suspension of compound 38 (0.57 g, 1.4 mmol) in water (10 mL) was cooled to 0° C. Concentrated HCl (0.6 mL) was added dropwise to give a yellow solution. After 10 min, sodium nitrite (0.22 g, 3.2 mmol) dissolved in water (2 mL) was added and the solution was stirred for 30 min at 0°. The solution was then poured into a solution of iodine (1 g, 3.9 mmol) and potassium iodide (1.0 g, 5.9 mmol) in water (100 mL). The solution was stirred at room temperature for 30 min. Extraction with ethyl acetate (200 mL), washing with 10% sodium hydrosulfate solution (100 mL), drying over $MgSO_4$, and evaporation of the solvent gave the crude diiodide (0.6 g). Recrystallization from hexanes/methylene chloride gave the pure product 39 (0.54 g, 63%) as a solid: mp 160–161° C. $^1$H NMR (300 MHz, $CDCl_3$) δ 8.37 (d, J=2.5 Hz, 2H), 8.27 (d, J=1.86 Hz, 2H), 4.07 (s, 6H), 3.95 (s, 6H); IR (neat) 3078, 2954, 1734, 1670, 1608, 1540 $cm^{-1}$. Anal. ($C_{19}H_{16}O_7I_2$) C, H.

3',3"-Diiodo-4',4"-Dimethoxy-5',5"-bis (methoxycarbonyl)-1,1-diphenyl-1-heptene (40). NaN$(TMS)_2$ (1 mL, 1 mmol) was added to an ice cold suspension of hexyltriphenylphosphonium bromide (0.427 g, 1 mmol) in THF (20 mL) and the solution was stirred for 30 min at 0° C. A solution of the benzophenone 39 (0.2 g, 0.33 mmol) in THF (5 mL) was added to the preformed ylide and the solution was stirred at rt overnight. The mixture was partitioned between 1 N HCl (100 mL) and ethyl acetate (100 mL). The organic layer was evaporated and flash chromatographed on $SiO_2$ (230–400 mesh, 50.0 g), eluting with hexanes-ethyl acetate (5:1). The fractions which contained the product were pooled, evaporated, and chromatographed on silica gel (230–400 mesh, 20 g), eluting with hexanes-ethyl acetate (5:1), to give the product 40 (0.022 g, 9%) as an oil: $^1$H NMR ($CDCl_3$, 300 MHz) δ 7.69 (s, 2H), 7.54 (d, J=2.0 Hz, 1H), 7.52 (d, J=2 Hz, 1H), 6.01 (t, J=7.6 Hz, 1H), 3.93 (s, 3H), 3.89 (s, 3H), 3.88 (s, 3H), 3.85 (s, 3H), 2.05 (q, J=7.3 Hz, 2H), 1.42 (m, 2H), 1.25 (m, 2H), 0.85 (t, J=6.7 Hz, 3H); IR (neat) 2953, 2929, 1742, 1738, 1731, 1713 $cm^{-1}$; HRFABMS calcd for $C_{25}H_{28}I_2O_6$ m/z 677.9975 ($M^+$). Found: m/z 677.9954. Anal. ($C_{25}H_{28}I_2O_6$·0.5EtOAc), C, H.

In Vitro Anti-HIV Assay. Anti-HIV screening of test compounds against various viral isolates and cell lines was performed as previously described. (Buckheit et al, *Antiviral Res.* 1995, 26, 117–132) This cell-based microliter assay quantitates the drug-induced protection from the cytopathic effect of HIV. Data are presented as the percent control of XTT values for the uninfected, drug-free control. $EC_{50}$ values reflect the drug concentration that provides 50% protection from the cytopathic effect of HIV-1 in infected cultures, while the $IC_{50}$ reflects the concentration of drug that causes 50% cell death in the uninfected cultures. XTT-based results were confirmed by measurement of cell-free supernatant reverse transcriptase and p24 levels.

Mechanistic Assays. The effects of inhibitors on the in vitro activity of purified RT (kind gift of Steve Hughes, NCI-FCRDC, Frederick, Md.) were determined by measurement of incorporation of $[^{32}P]TTP$ into the poly(rA):oligo (dT) (rAdT) homopolymer or $[^{32}P]GTP$ into the poly(rC):oligo(dG) (rCdG) template/primer systems. Samples (5 μL) were blotted onto DE81 paper, washed with 5% diabasic sodium phosphate, and then quantitated on a Packard Matrix 9600 direct beta counter. 3'-Azido-2',3'-dideoxythymidine-5'-triphosphate (AZTTP) and NSC 629243 (UC38) served as a positive control for inhibition of RT.

To determine if compounds affected the HIV-1 nucleocapsid protein zinc fingers, fluorescence measurements of the Trp[37] residue in the C-terminal zinc finger of the HIV-1 nucleocapsid protein were performed as previously described. (Rice et al. *Science*, 1995, 270, 1194–1197). The recombinant nucleocapsid protein was prepared at 20 μg/mL in 10 mM sodium phosphate buffer (pH 7.0), treated with 25 μM of test compound, then after indicated time intervals the samples were diluted 1/10 in 10 mM sodium phosphate buffer (pH 7.0) and the fluorescence intensity measured. The excitation and emission wavelengths utilized with the Shimadzu RF5000 spectrofluorimeter were 280 and 351 mm, respectively. The analytical procedure employed to determine the reagent-induced inhibition of HIV-1 protease activity has been previously described. Recombinant HIV-1 protease (Bachem BioScience Inc., King of Prussia, Pa.) and the substrate (Val-Ser-Gln-Asn-Tyr-Pro-Ile-Val-Gln-$NH_2$, Multiple Peptide Systems, San Diego, Calif.) were utilized to determine the concentration of test compound required to inhibit protease activity by 50% ($IC_{50}$). Briefly, HIV-1 protease (14.2 nM final) was mixed with various concentrations of test compounds in 250 mM potassium phosphate buffer, pH 6.5, 2.5% (v/v) glycerol, 0.5 mM dithiothreitol, 0.5 mM EDTA and 375 mM ammonium sulfate, after which the substrate was added (30 nmol) and the reaction incubated at 37° C. for 30 min. Reactions were terminated by the addition of 20 pL of a mixture of 8 M guanidine-HCl to 10% trifluoroacetic acid (8:1), and the reaction products were separated by reverse-phase HPLC on a Nova-Pak C-18 column. Absorbance was measured at 206 nm, peak areas quantitated, and the percentage conversion to product used to calculate the percentage of control cleavage in the presence of inhibitors. The 3'-cleavage and integration activities of purified HIV-1 integrase were quantitated as previously described. (Rice *PNAS* 1993, 90, 9721–9724).

The attachment/fusion assay was performed as described by Ciminale (*AIDS Res. Hum. Retrovir.* 1990, 6, 1281–1287) with modification. Briefly, HIV-1 envelope-expressing, Tat-producing HL2/3 cells and CXCR-4 expressing, LTR-βGal-containing MAGI cells (obtained from the AIDS Research and Reference Program, National Institute of Allergy and Infectious Disease, NIH, Bethesda, Md., USA) were preincubated separately with test compound for 1 h at 37° C., followed by admixture of the two cell lines at a cell ratio of one to one. Incubations were then continued for 16 h. The cells were then fixed and stained for the expression of β-gal with indolyl-β-D-galactopyranoside (X-Gal). The number of blue cells (indicating completion of attachment and fusion of membranes) were counted by light microscopy.

Other examples of the preparation of compounds in accordance with this invention are illustrated in the following reaction schemes:

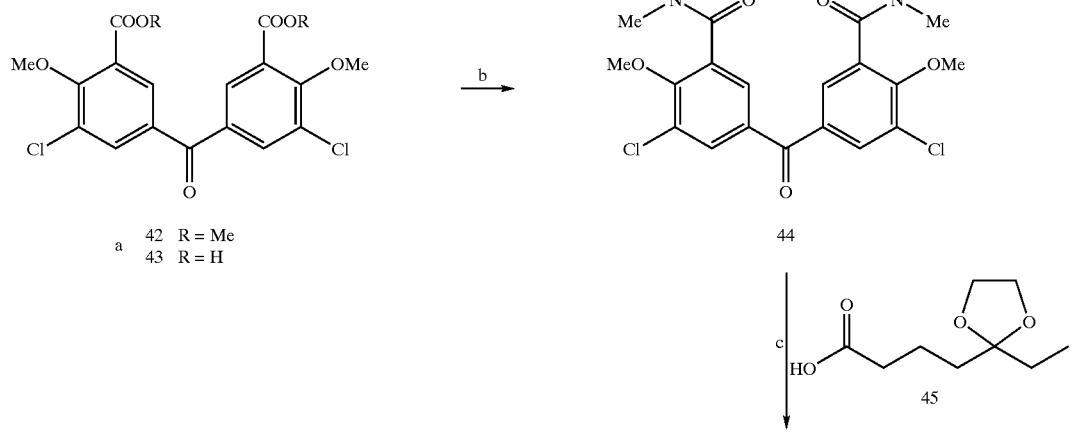

Scheme 2[a]

-continued

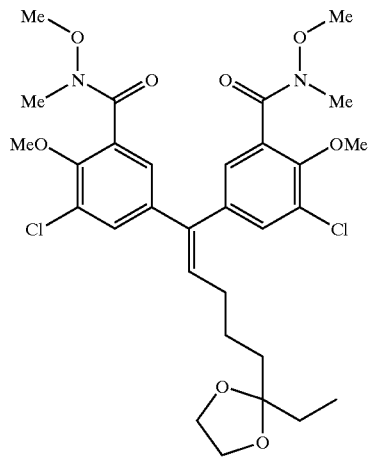

46

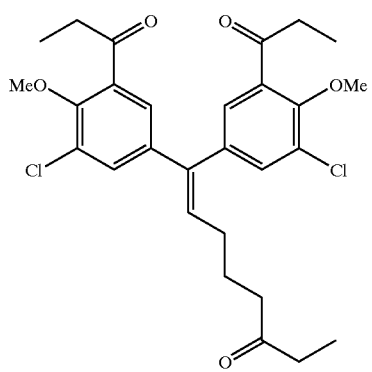

47

ᵃReagents and conditions: (a) K₂CO₃, KCN, THF—MeOH—H₂O, 75° C., 5 h, 97.8%; (b) i: (COCl)₂, cat. DMF, THF, rt, 4 h; ii: MeONH(Me)—HCl, Pyr, CH₂Cl₂, rt, 12 h, 56.9%; (c)TiCl₄—THF (1:2), Zn(0), THF, reflux, 2 h; then 4, THF, 3 h, 17%; (d) i: EtLi, THF—Et₂O, -78° C., 3 h; ii: H₃O⁺, 12 h.

Scheme 3ᵃ

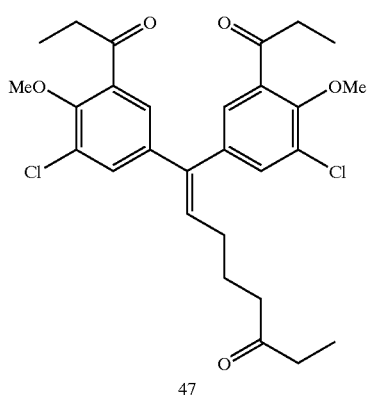

47

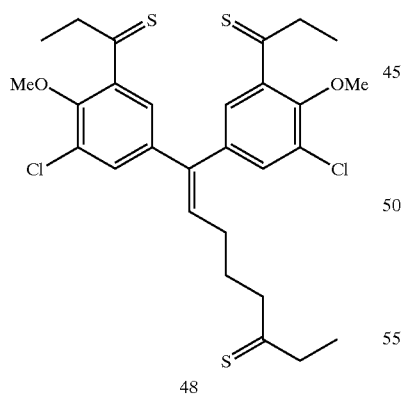

48

ᵃReagents and Conditions: (a) (R₃Sn)₂S (R = cyclohexyl), BCl₃.

Scheme 4ᵃ

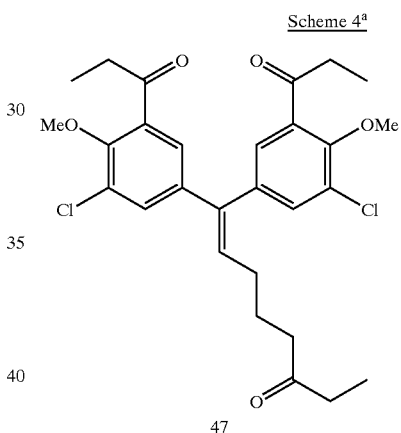

47

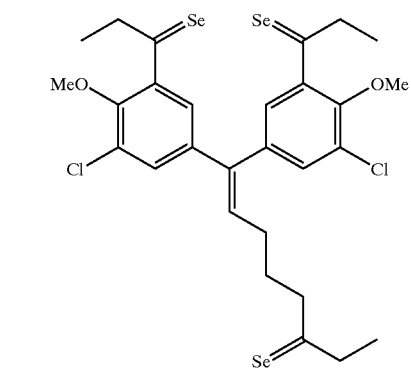

49

ᵃReagents and Conditions: (a) (R₃Sn)₂S (R = cyclohexyl), BCl₃.

Reference: Steliou, K., Mrana, M. "Tin-Assisted Sulfuration. A Highly Potent New Method for the Conversion of Carbonyl Units into Their Corresponding Thiocarbonyl Analogues" *J. Am. Chem. Soc.* 1982, 104, 3104–3106.

Reference: Steliou, K., Mrana, M. "Tin-Assisted Sulfuration. A Highly Potent New Method for the Conversion of Carbonyl Units into Their Corresponding Thiocarbonyl Analogues" *J. Am. Chem. Soc.* 1982, 104, 3104–3106.

Scheme 5

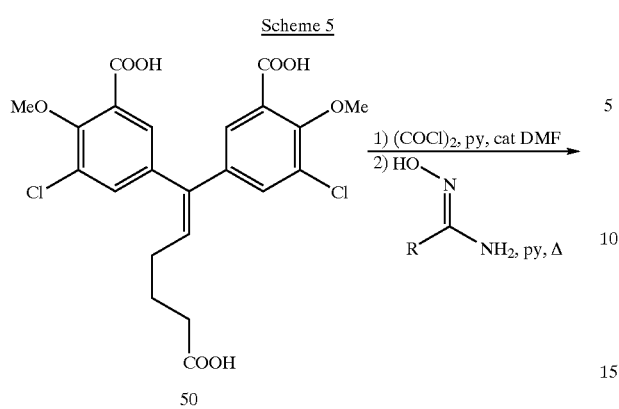

50

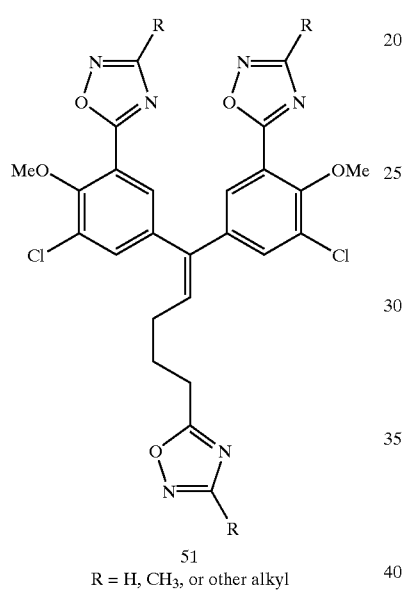

51
R = H, CH₃, or other alkyl

Reference: Orlek, Barry S.; Blaney, Frank E.; Brown, Frank; Clark, Michael S. G.; Hadley, Michael S.; Hatcher, John.; Riley, Graham J.; Rosenberg, Howard E.; Wardsworth, Harry J.; Wyman, Paul "Comparison of Azabicyclic Esters and Oxadiazoles as Ligands for the Muscarinic Receptor" *J. Med. Chem.* 1991, 34, 2726–2735.

Scheme 6

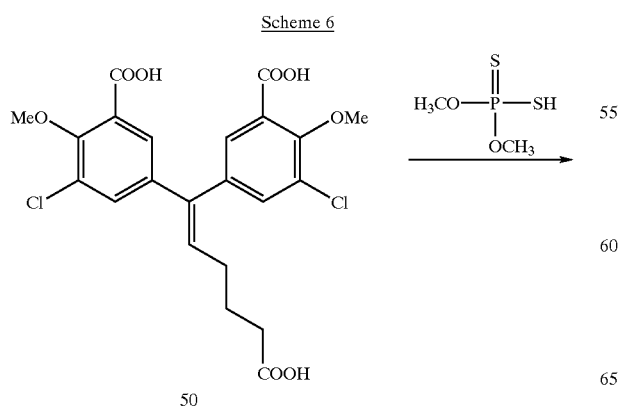

50

-continued

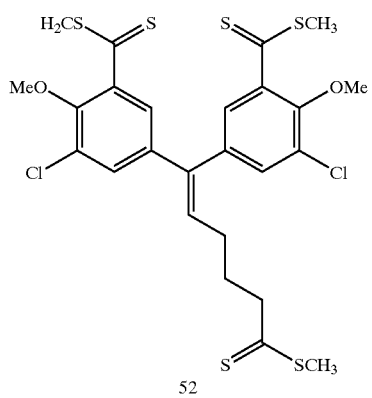

52

Reference: Yousif, N. M. "The Reaction of Carboxylic Acid Chlorides with O,O-Dialkyldithiophosphoric Acids" *Phosphoris, Sulfur Silicon Relat. Elem.* 1989, 46, 79–81.

Scheme 7

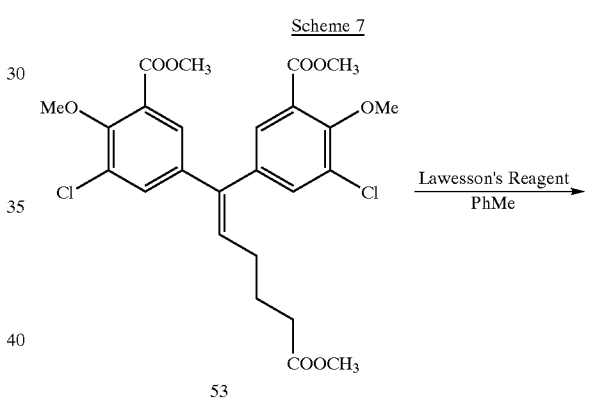

53

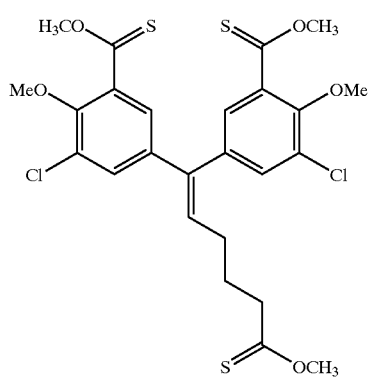

54

Reference: Bunnelle, W. H.; McKinnis, B. R.; Narayanan, B. A. "Difluorination of Esters. Preparation of α,α-Difluoro Ethers," *J. Org. Chem.* 1990 55, 768–770.

Scheme 8

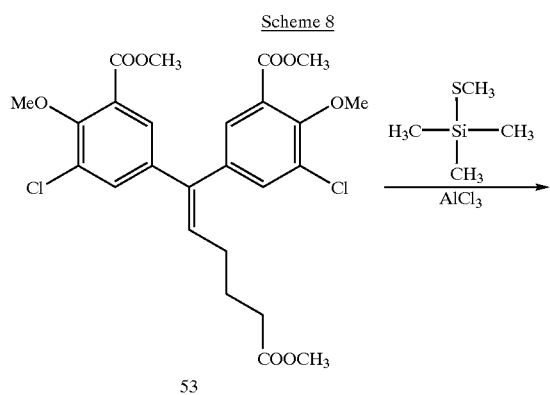

Scheme 9

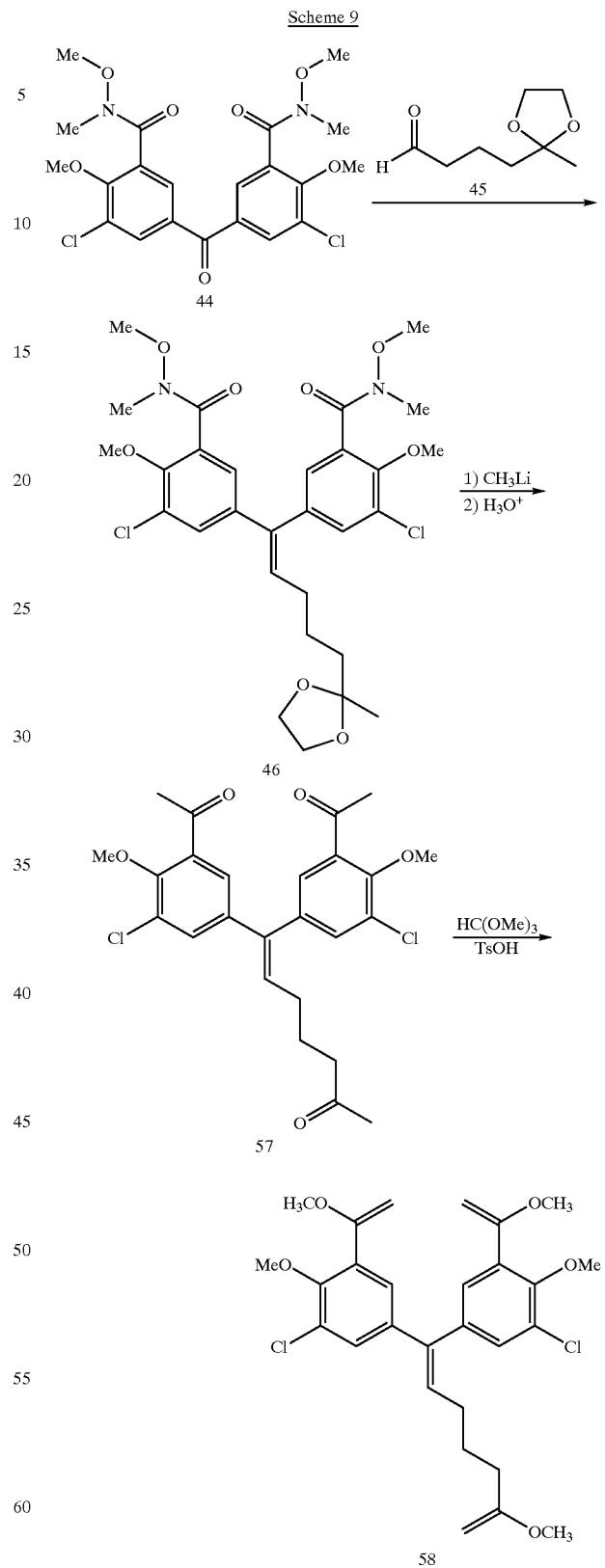

References: Matthews, Donald P.; Whitten, Jeffrey P.; McCarthy, James R. "A facile synthesis of aromatic trifluoromethyl compounds via orthothioesters" *Tetrahedron Lett.* 1986, 27, 4861–4; Barbero, Margherita; Cadamuro, Silvano; Degani, Iacopo; Fochi, Rita; Gatti, Antonella; Regondi, Valeria "Simple procedures for the hydrolysis of trimethyl trithioorthocarboxylates to methyl thiolcarboxylates. A convenient route to electron-rich aromatic and heteroaromatic methyl thiolcarboxylates" *Synthesis* 1988, 300–2.

Reference: Ben-David, I.; Michani, E.; Rozen, S. "tert-Butyl Hypofluorite-An Electronic tert-Butoxylation Agent," *J. Org. Chem.* 1998, 63, 4632–4635.

Scheme 10

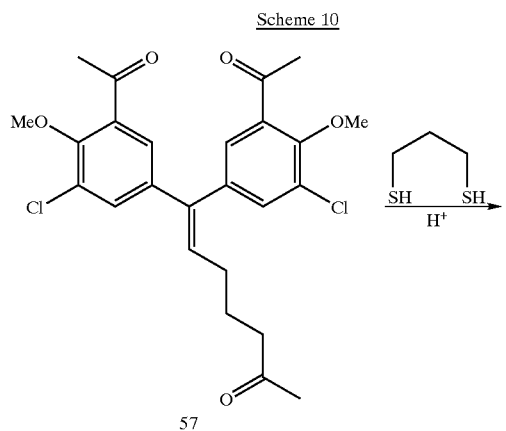

57

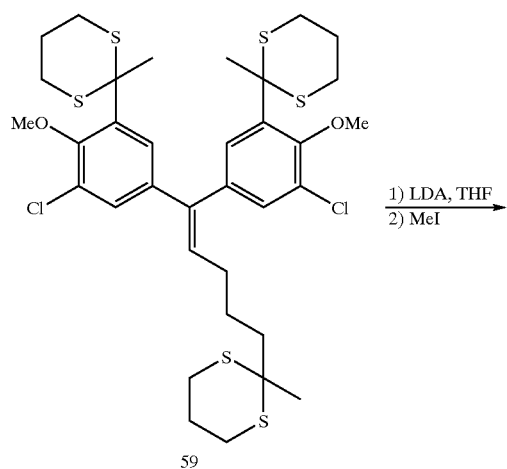

59

1) LDA, THF
2) MeI

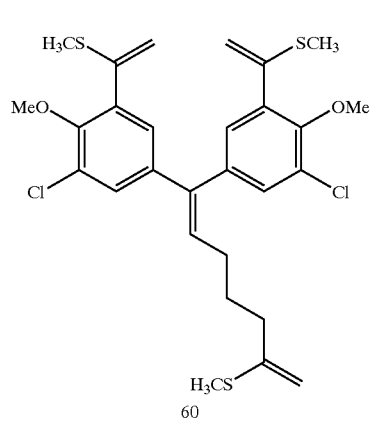

60

References: Willmore, Nikolaos D.; Hoic, Diego A.; Katz, Thomas J. "Diels-Alder Reactions of α-Substituted Styrenes with p-Benzoquinone" *J. Org. Chem.* 1994, 59, 1889–91. Ikehira, Hideyuki; Tanimoto, Shigeo; Oida, Tatsuo. "The Lithium Diisopropylamide-Induced Fragmentation of 1,3-Dithiolane Derivatives of Several Ketones Having α-Hydrogen" *Bull. Chem. Soc. Jpn.* 1983, 56, 2537–8.

Scheme 11

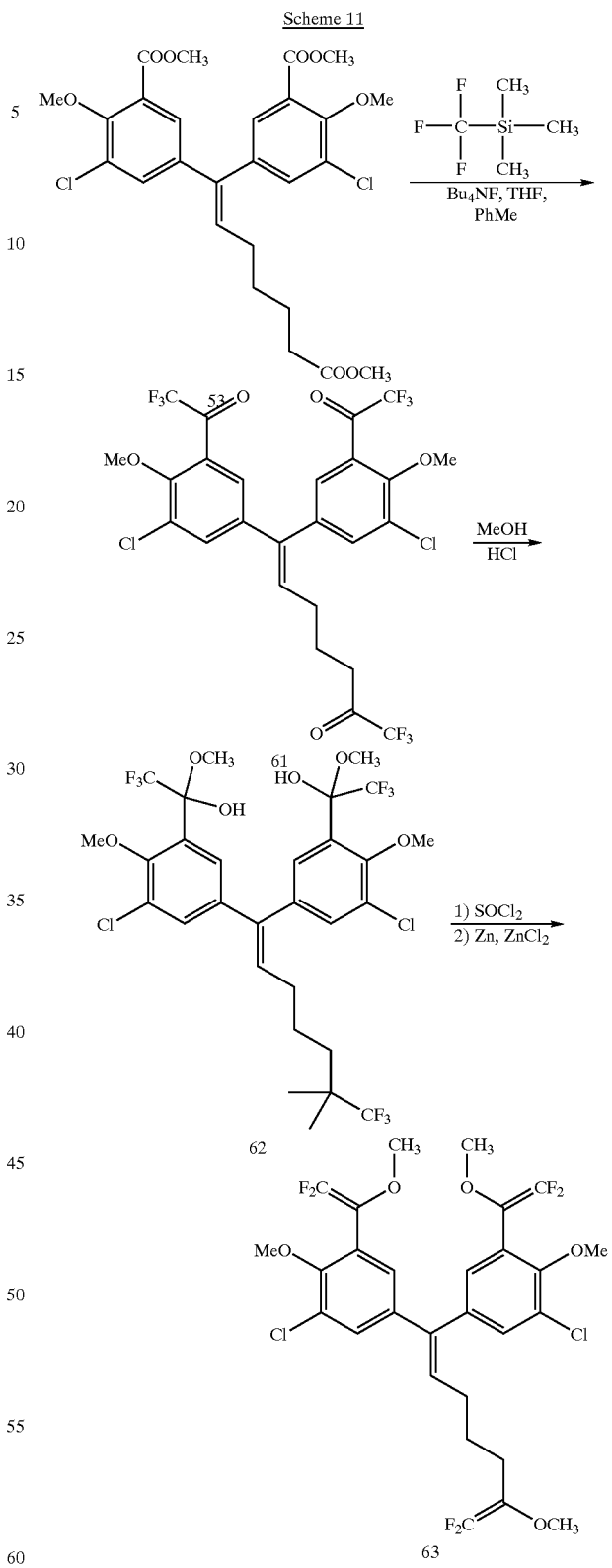

References: Wiedemann, Jurgen; Heiner, Thomas; Mloston, Gregorz; Prakash, G. K. Surya; Olah, George A. "Synthetic methods and reactions. Part 201. Direct preparation of trifluoromethyl ketones from carboxylic esters: trifluoromethylation with (trifluoromethyl)trimethylsilane" *Angew. Chem., Int. Ed.* 1998, 37, 820–821. Bekker, R. A.; Asratyan, G. V.; Dyatkin, B. L.; Knunyants, I. L. "Polyhalogenated α-oxides. VI. Synthesis of α-substituted difluoroacrylic acids and alkyldifluorovinyl ethers from polyfluorinated α-oxides" *Zh. Org. Khim.* 1975, 11, 961–5.
Scheme 12
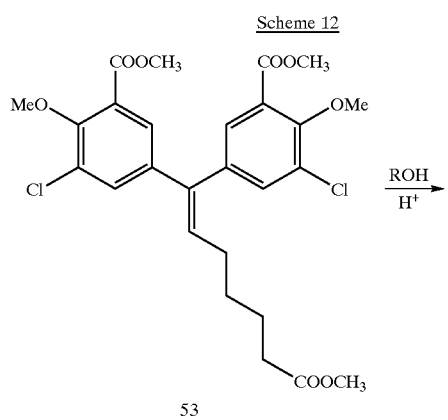
53
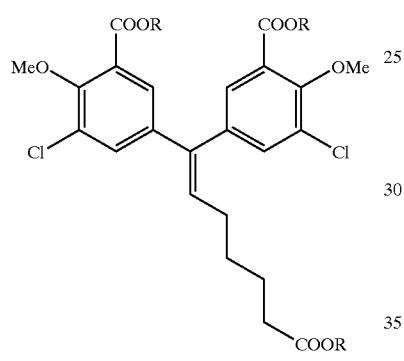
64 R = Et
65 R = i-Pr
66 R = tBu
Scheme 13
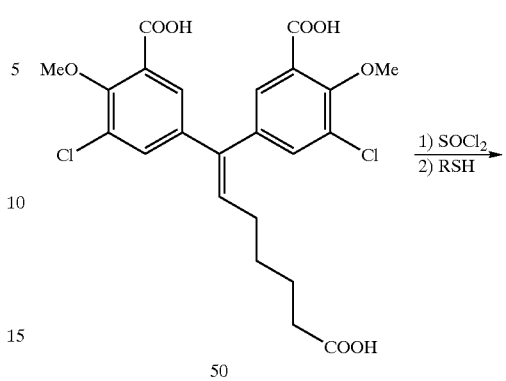
50
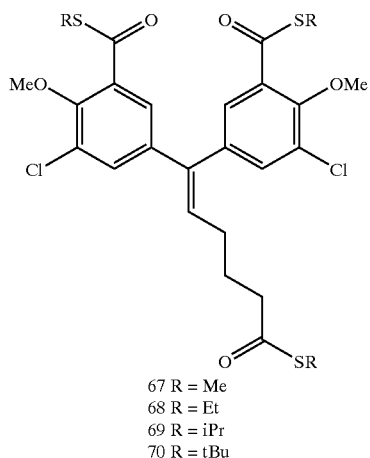
67 R = Me
68 R = Et
69 R = iPr
70 R = tBu
Scheme 14
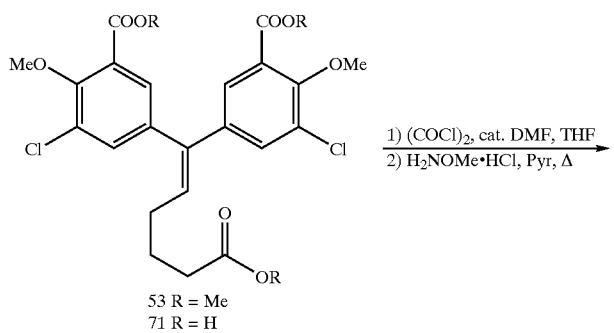
53 R = Me
71 R = H
K₂CO₃, KCN,
THF—MeOH—H₂O
75° C.
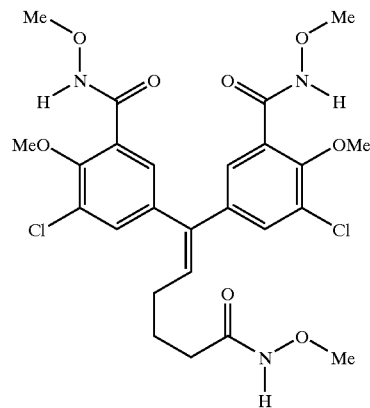
72
PPh₃, CX₄, CH₃C
(X = Cl or Br)

-continued

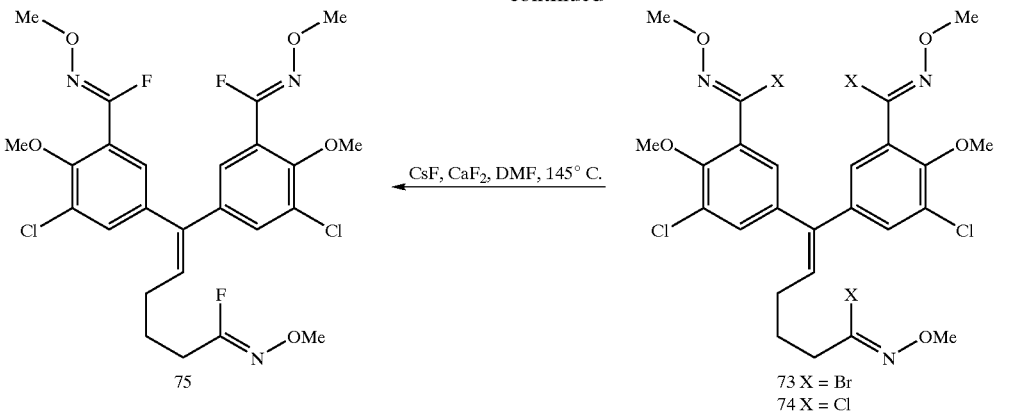

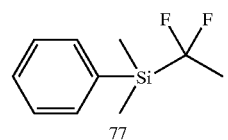

Reference: Bromidge, Steven M.; Brown, Frank; Cassidy, Frederick; Clark, Michael S. G.; Dabbs, Steven; Hadley, Michael S; Loudon, Julia M.; Naylor, Christopher B.; Orlek, Barry S. "Design of [R-(Z)-(+)-α-(Methoxyimino)-1-azabicyclo[2.2.2]octane-3-acetonitrile (SB 202026), a Functionally Selective Azabicyclic Muscarinic M1 Agonist Incorporating the N-Methoxy Imidoyl Nitrile as a Novel Ester Bioisostere" *J. Med. Chem.* 1997, 40, 4265–4280.

Scheme 15

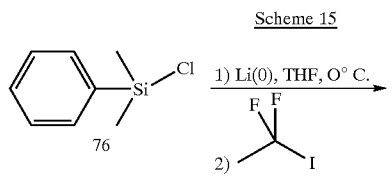

References: Marival-Hodebar, Laurence; Tordeux, Marc; Wakselman, Claude "A Convenient Access to 1,1-Difluoroethyl Triflate and Iodide" *J. Chem. Research* (S) 1998, 192–193. Fuchikami, Takamasa; Ojima, Iwao "Reaction of (Bromodifluoromethyl)-phenyldimethylsilane With Organometallic Reagents" *Journal of Organomet. Chem.* 1981, 212, 145–153.

Scheme 16

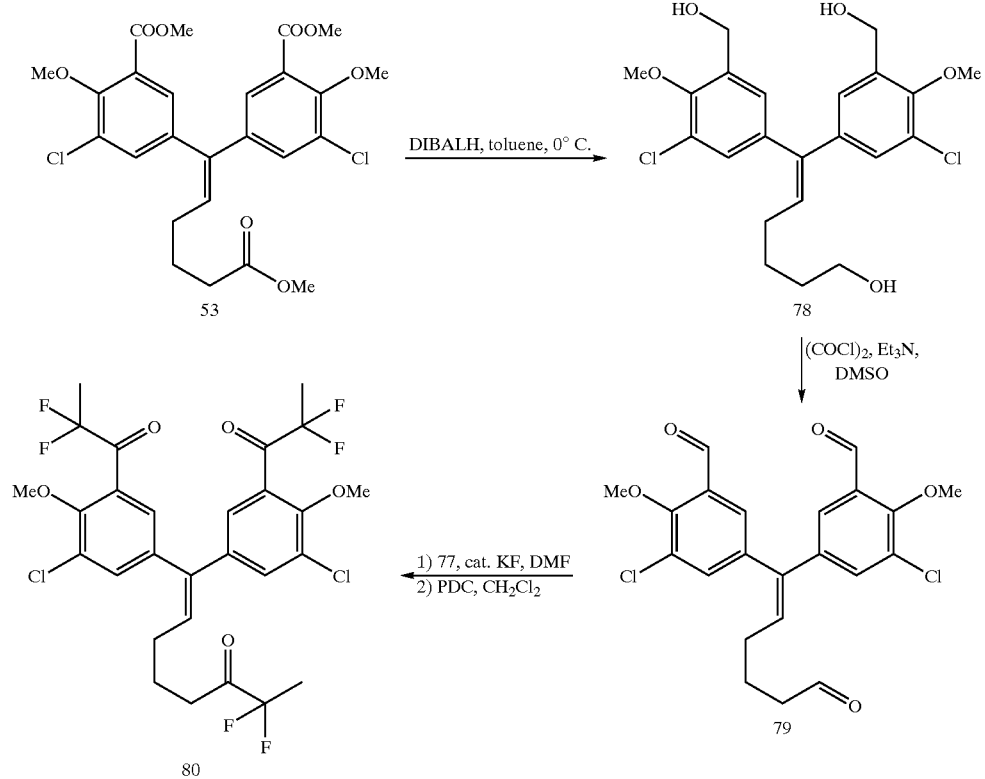

Reference: Hagiwara, Toshiki; Fuchikami, Takamasa "Difluoroalkylation of Carbonyl Compounds with (1,1-Difluoroalkyl)silane Derivatives" *Synlett* 1995, 717–718.

Scheme 17

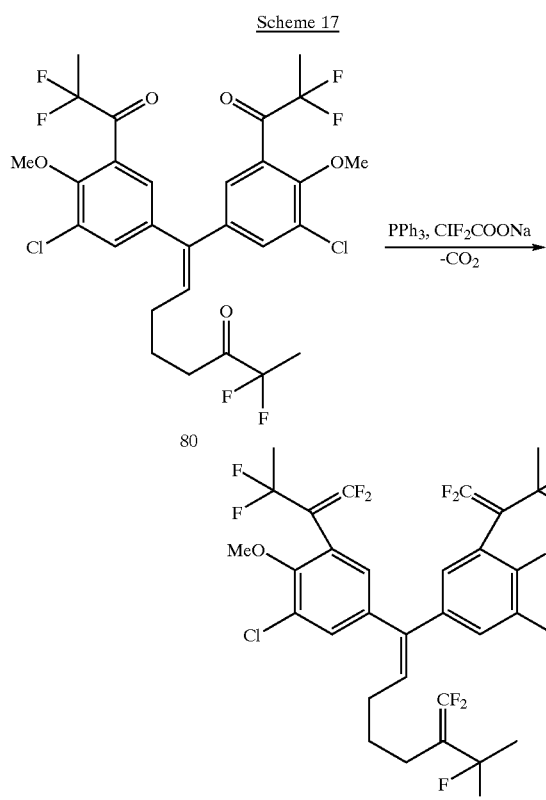

Reference: Herkes, Frank E.; Burton, Donald J. "Fluoro Olefins. I. The Synthesis of β-Substituted Perfluoro Olefins" *J. Am. Chem. Soc.* 1967, 89, 1311–1318.

Scheme 18

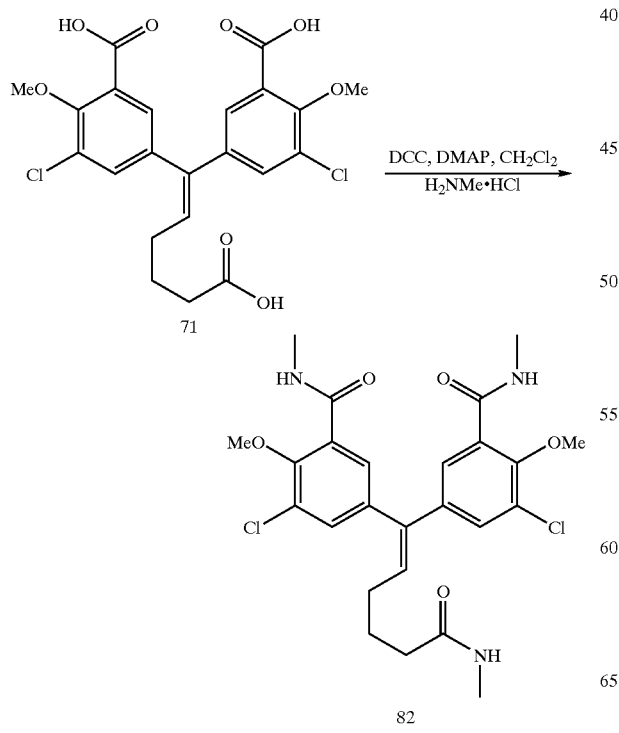

Scheme 19

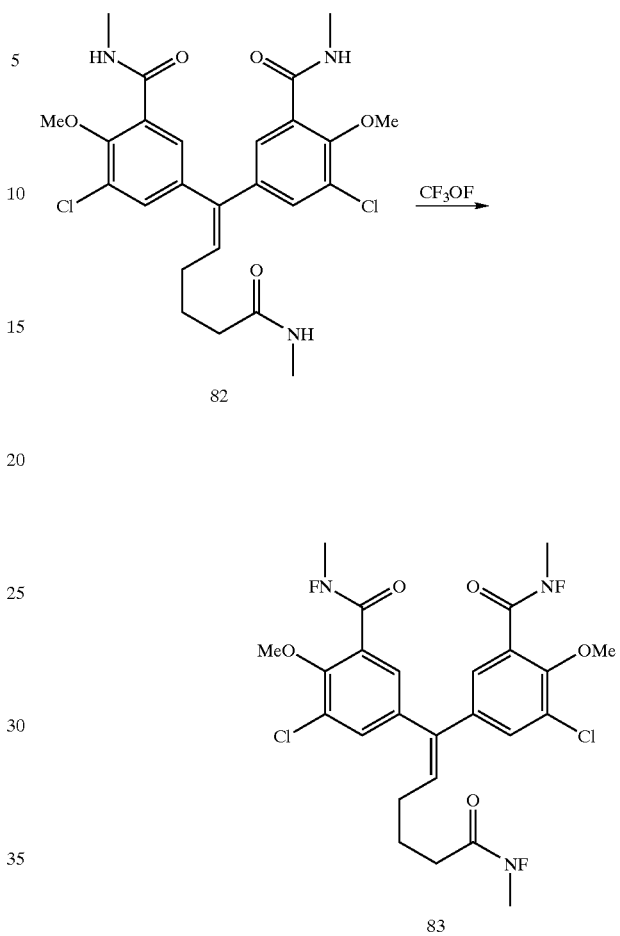

Reference: Hammer, Charles F.; Chandrasegaran, Srinivasan "Determination of $J_{HF}$ and $^4J_{HF}$ Karplus Relationships for the φ and ψ Angles of Peptides Using N-Fluoroamides as Models" *J. Am. Chem. Soc.* 1984, 106, 1543–1552.

Scheme 20

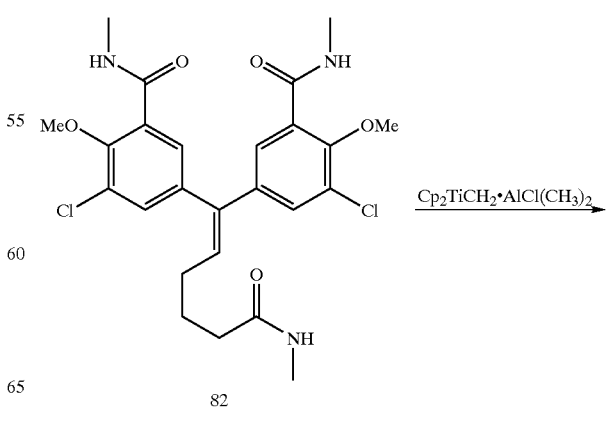

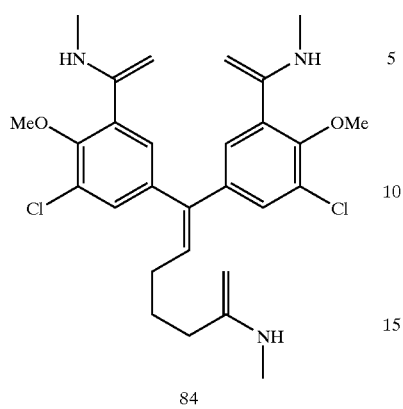
Reference: Pine, Stanley H.; Pettit, Robert J.; Geib, Gregory D.; Cruz, Susana G.; Gallego, Cladio H.; Tijerina, Thomas; Pine, Randall D. "Carbonyl Methylenation Using a Titanium-Aluminum (Tebbe) Complex" *J. Org. Chem.* 1985, 50, 1212.
Scheme 21
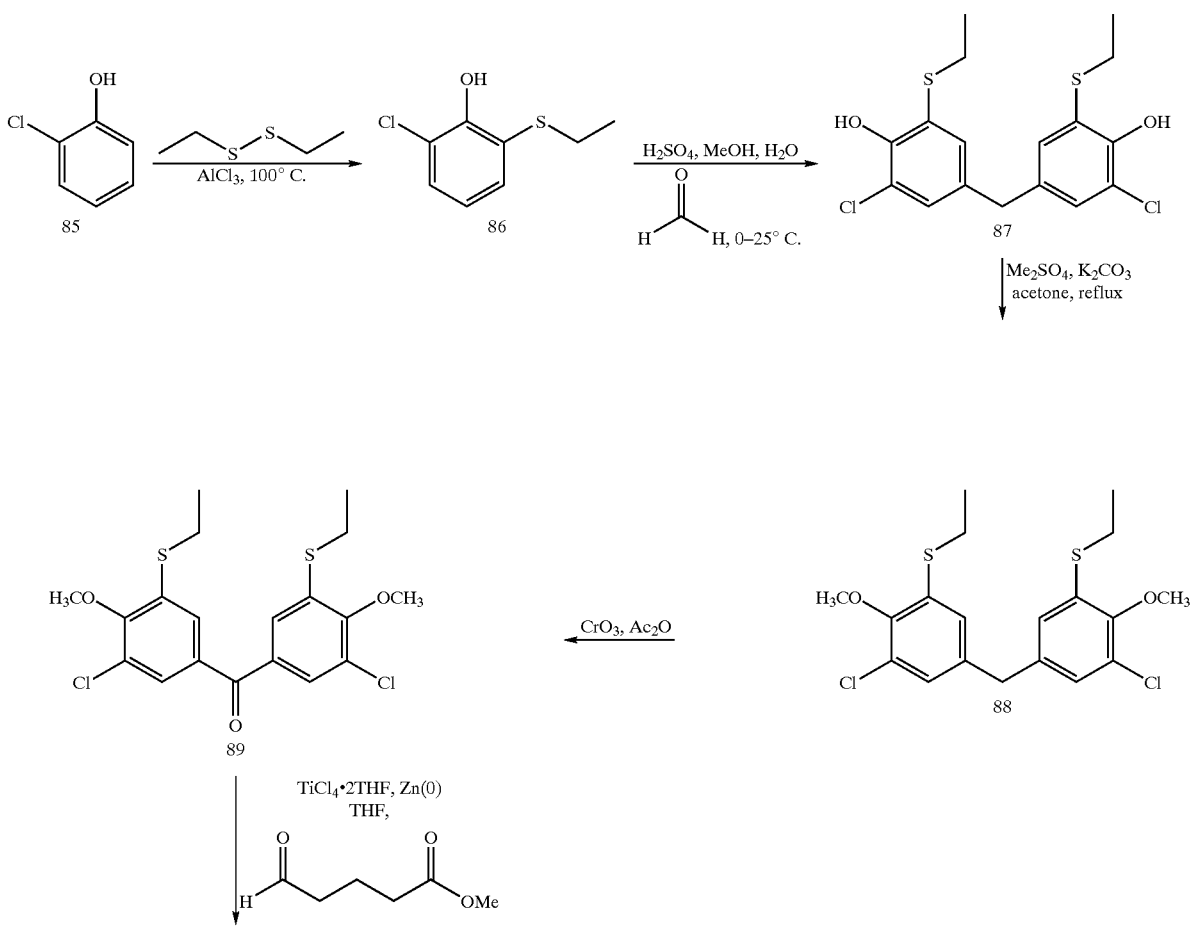

45

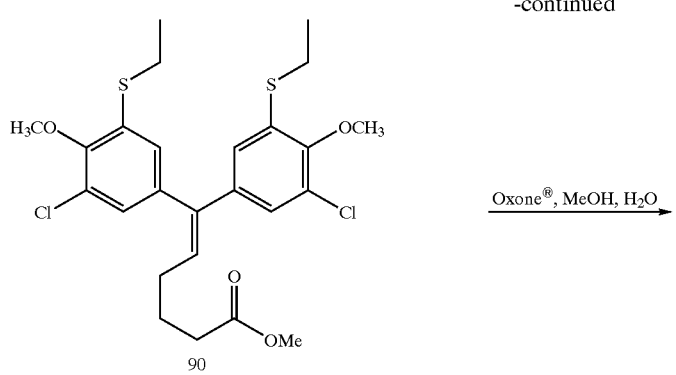

90

46

-continued

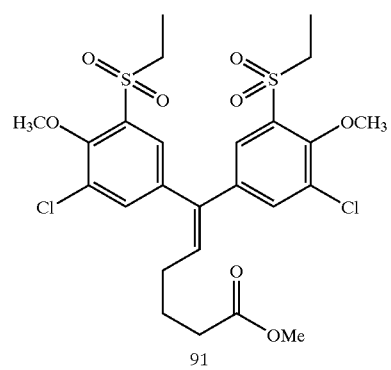

91

References: Morita, Yasushi; Kashagi, Atsushi; Nakasuji, Kazzuhiro "First Synthesis of Alkythio-Substituted (4-4'-Biphenoquinones and 4-4'-Biphenohydroquinones (4-4'-Biphenyldiols)," J. Org. Chem. 1997. 62, 7464–7468. Pennin, T. D.; Kramer, S. W.; Lee, Len F.; Collins, Paul W.; Koboldt, Carol M.; Seibert, Karen; Veenhuizen, Amy W.; Zhang, Yan Y.; Isakson, Peter C. "3,4-Diarylpyrazoles: Potent and Selective Inhibitors of Cyclooxgenase-2" Bioorg. Med. Chem. Lett. 1997, 7, 2121–14.

Scheme 22

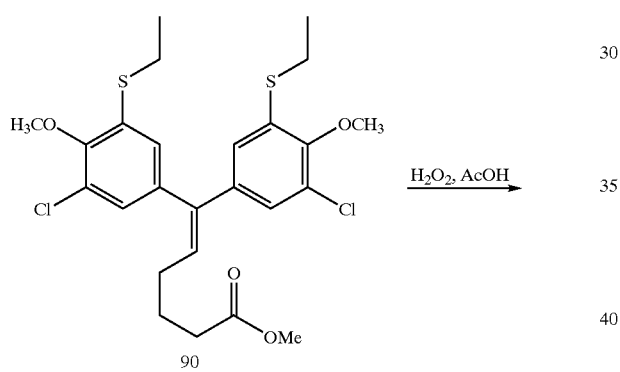

90

-continued

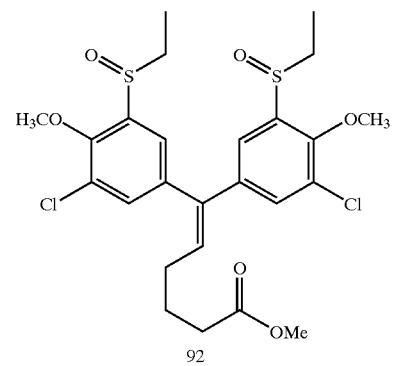

92

Scheme 23

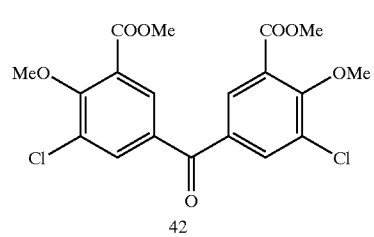

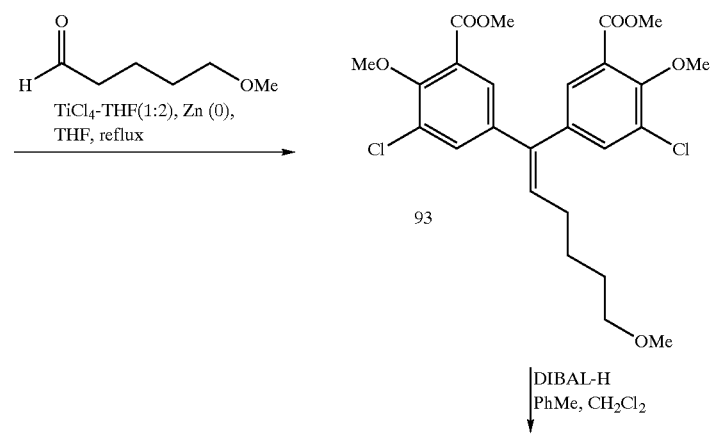

93

DIBAL-H
PhMe, CH$_2$Cl$_2$

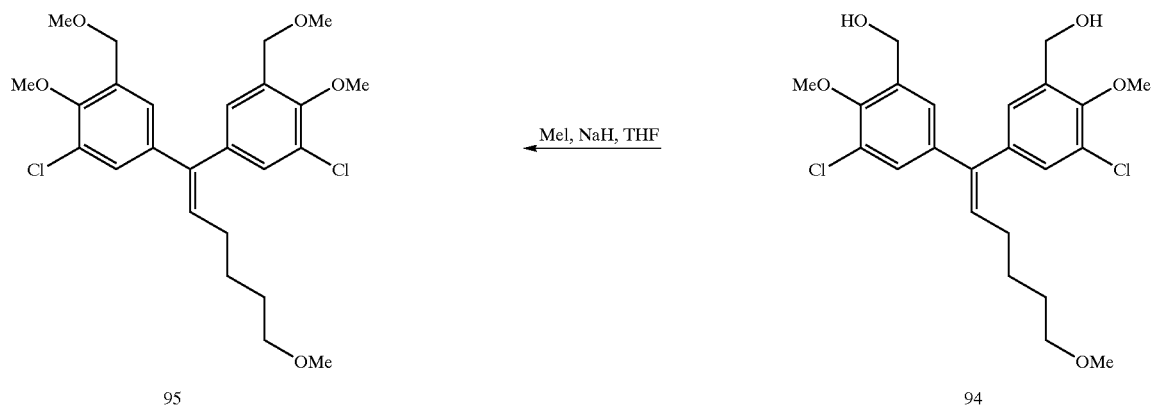
-continued
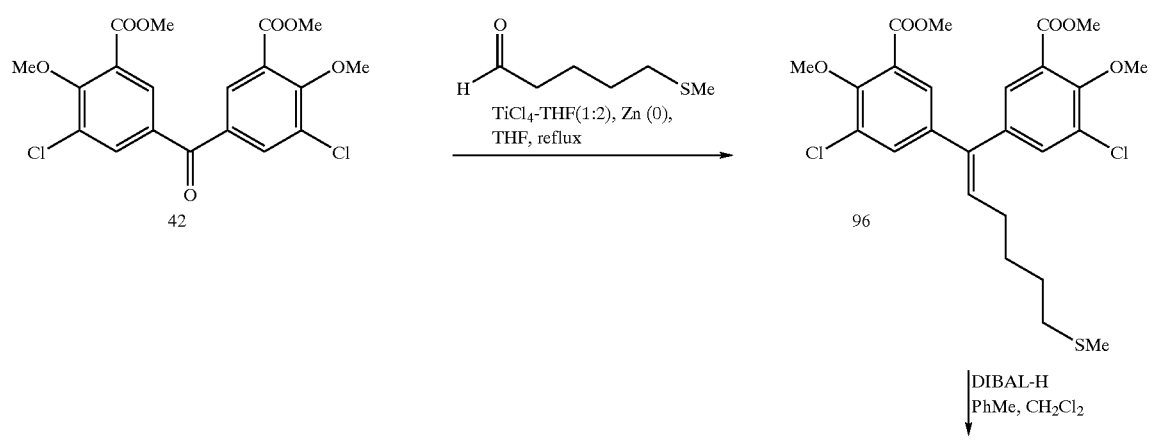
Scheme 24
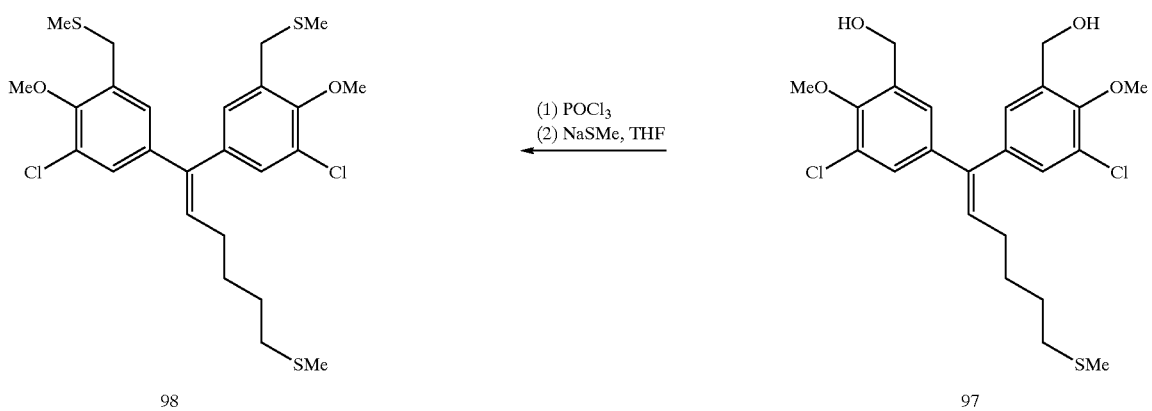

Scheme 25
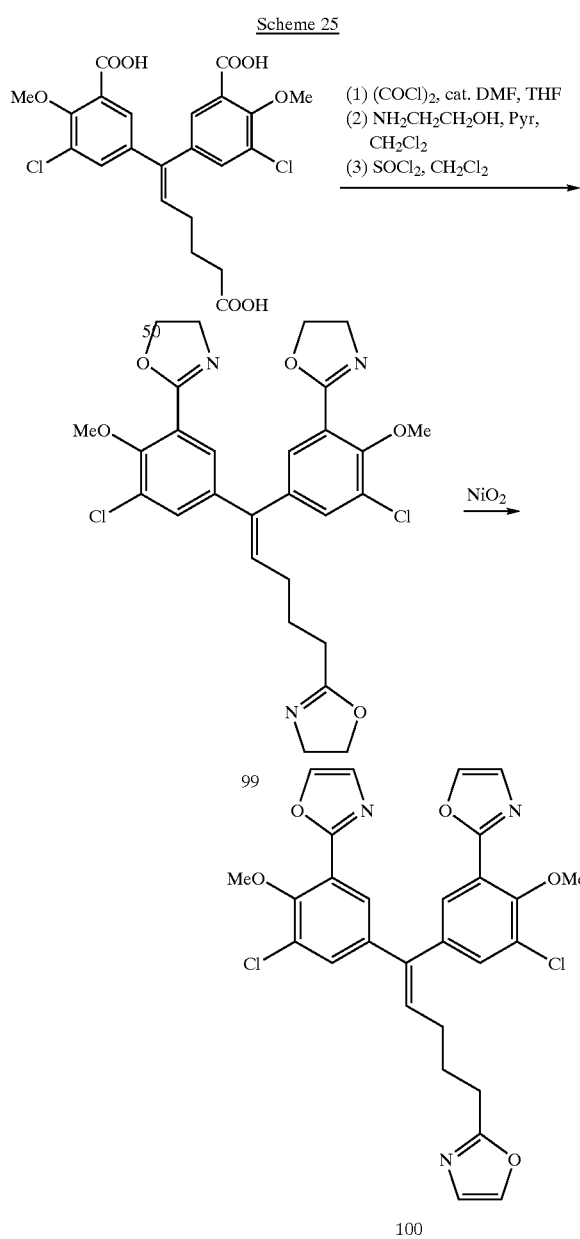
Scheme 26
Reference: Reuman, M., Meyers, A. I. "The Synthetic Utility of Oxazolines in Aromatic Substitution" *Tetrahedron* 1985, 41, 837–860.
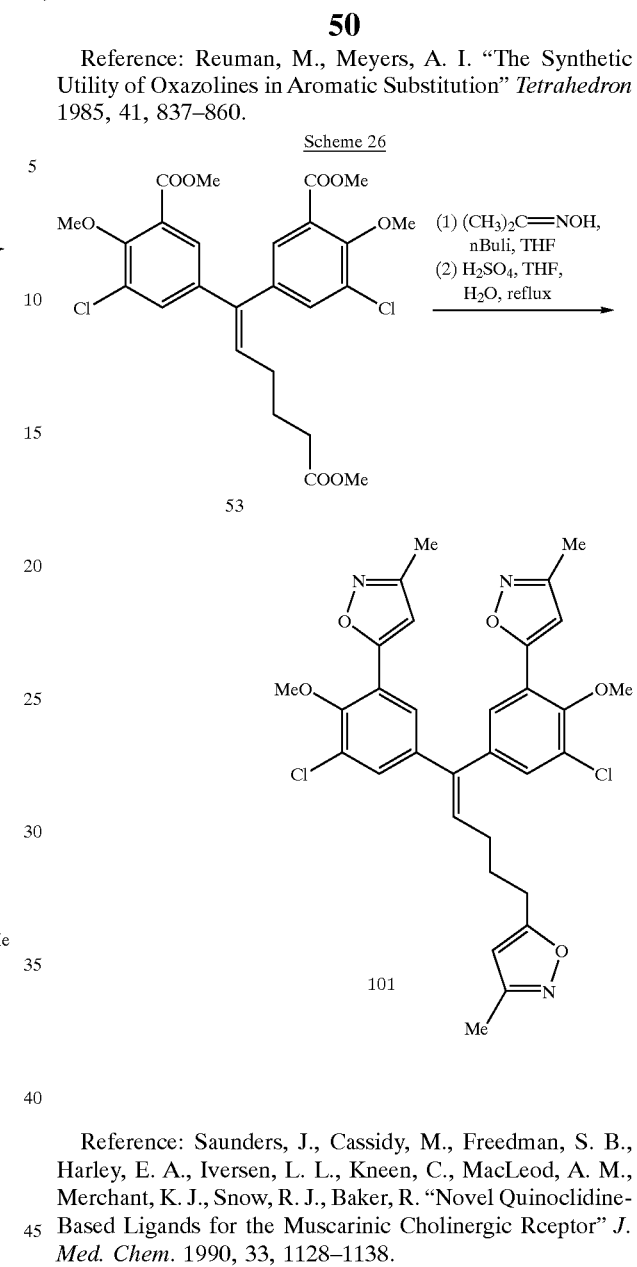
Reference: Saunders, J., Cassidy, M., Freedman, S. B., Harley, E. A., Iversen, L. L., Kneen, C., MacLeod, A. M., Merchant, K. J., Snow, R. J., Baker, R. "Novel Quinoclidine-Based Ligands for the Muscarinic Cholinergic Receptor" *J. Med. Chem.* 1990, 33, 1128–1138.
Scheme 27
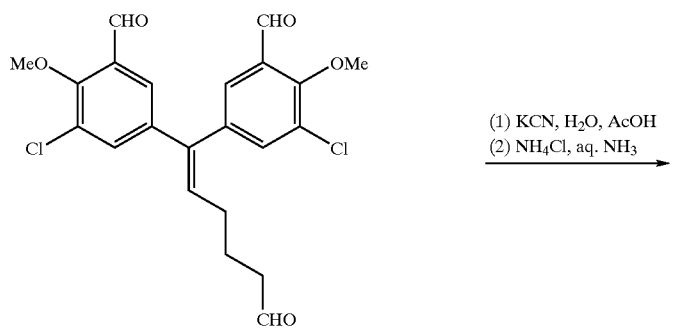

51
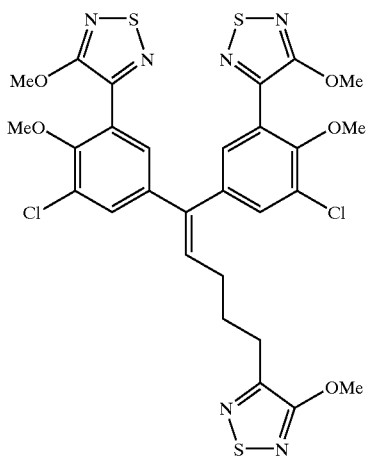
104
52
-continued
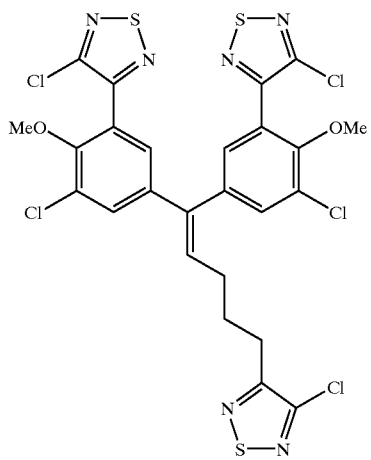
103
NaOMe, MeOH
Reference: Sauerberg, P., Olesen, P. H., Nielsen, S., Treppendahl, S., Sheardown, M. J., Honore, T., Mitch, C. H., Ward, J. S., Pike, A. J., Bymaster, K. P., Sawyer, B. D., Shannon, H. E. "Novel Functional $M_1$ Selective Muscarinic Agonists. Synthesis and Structure-Activity Relationships of 3-(1,2,5-Thiadiazolyl)-1,2,5,6-tetrahydro-1-methylpyridines" *J. Med. Chem.* 1992, 35, 2274–2283.
Scheme 28
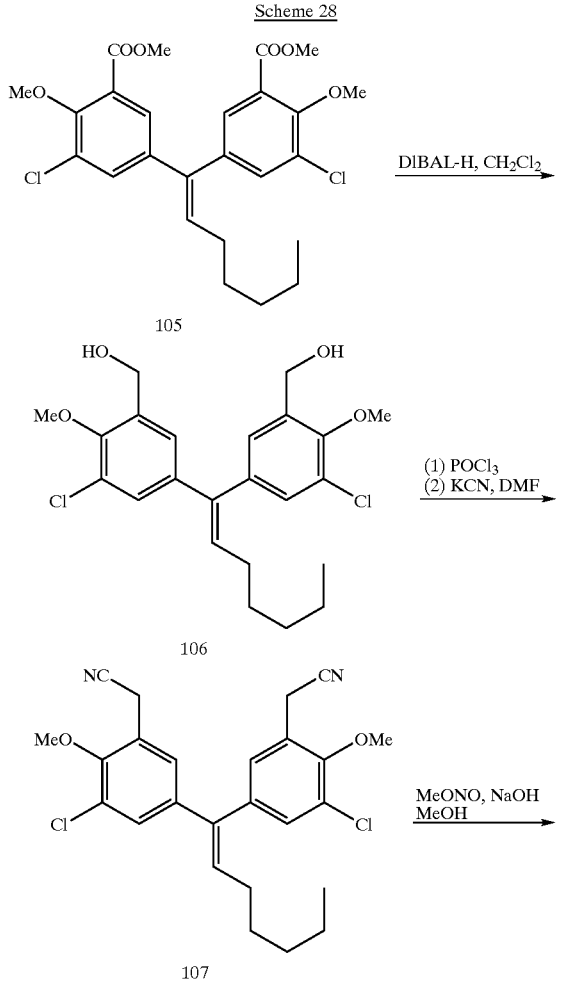
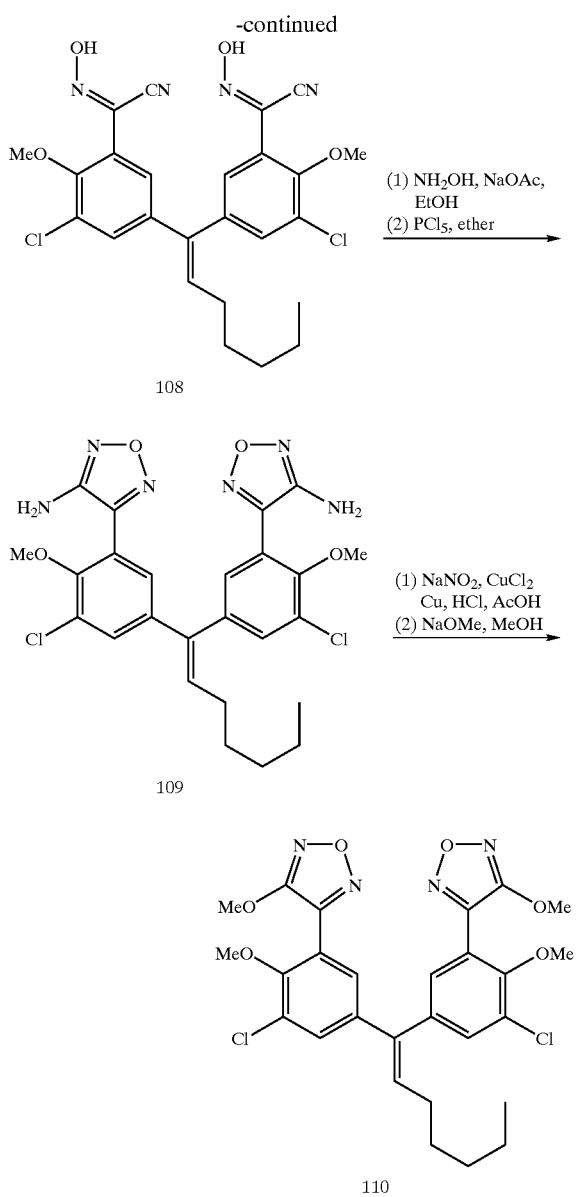

Reference: Sauerberg, P., Olesen, P. H., Nielsen, S., Treppendahl, S., Sheardown, M. J., Honore, T., Mitch, C. H., Ward, J. S., Pike, A. J., Bymaster, K. P., Sawyer, B. D., Shannon, H. E. "Novel Functional $M_1$ Selective Muscarinic Agonists. Synthesis and Structure-Activity Relationships of 3-(1,2,5-Thiadiazolyl)-1,2,5,6-tetrahydro-1-methylpyridines" *J. Med. Chem.* 1992, 35, 2274–2283.

Scheme 29

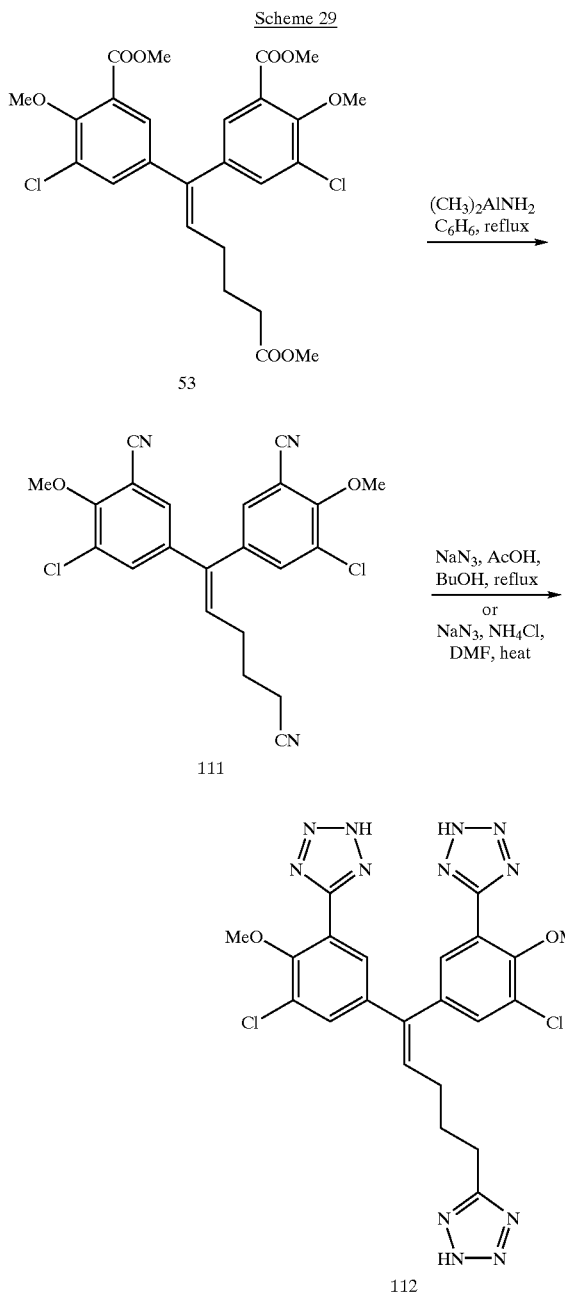

Scheme 30

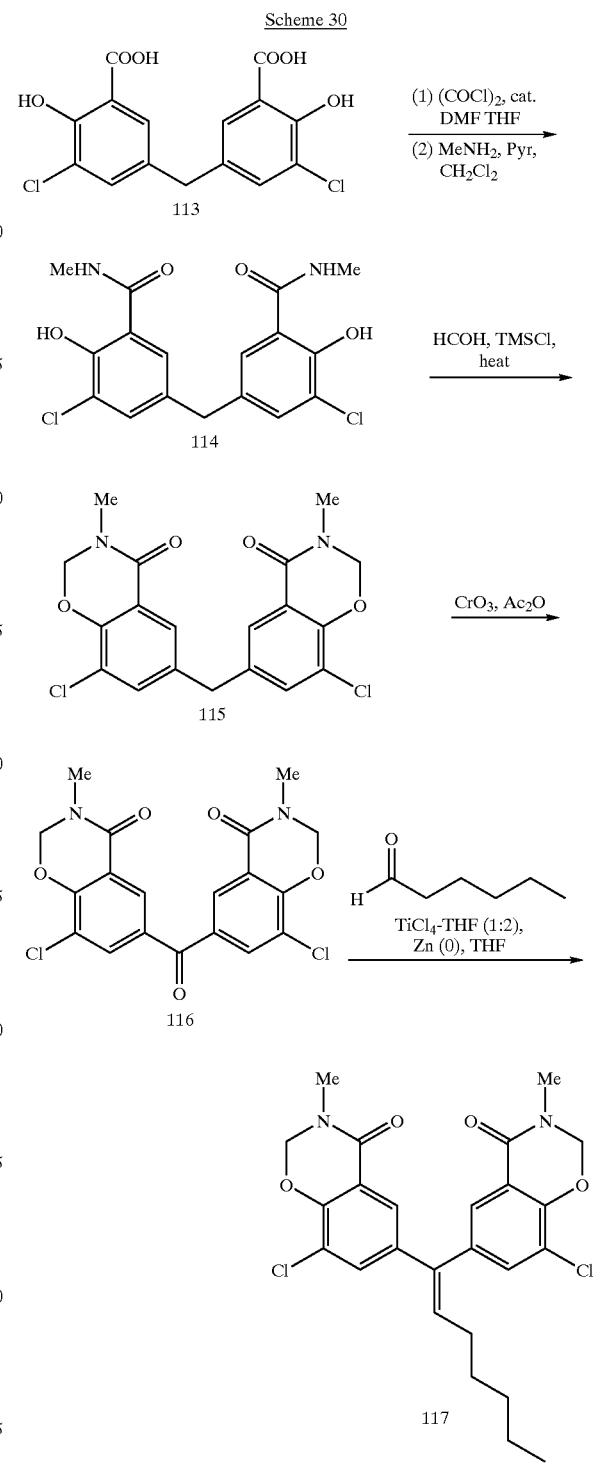

References: Wood, J. L., Khatri, N. A., Weinreb, S. M. "A Direct Conversion of Esters to Nitriles" *Tet. Lett.* 1979, 4907–4910; Moltzen, E. K., Pedersen, H., Bogeso, K. P., Meier, E., Frederiksen, K., Sanchez, C., Lembol, H. L. "Bioisosteres of Arecoline: 1,2,3,6-Tetrahydro-5-pyridyl-Substituted and 3-Piperidyl-Substituted Derivatives of Tetrazoles and 1,2,3-Triazoles. Synthesis and Muscarinic Activity" *J. Med. Chem.* 1994, 37, 4085–4099.

Reference: Shipov, A. G., Orlova, N. A., Kobzareva, V. P., Mozzhukhin, A. O., Antipin, M. Yu., Struchkov, Yu. T., Baukov, Yu. I. "Trimethylchlorosilane-carbonyl Compound System in Synthesis of Heterocyclic Compounds from Hydroxy and Aminoacid Derivatives" *Zh. Obshch. Khim.* 1993, 63, 371–377.

Scheme 31

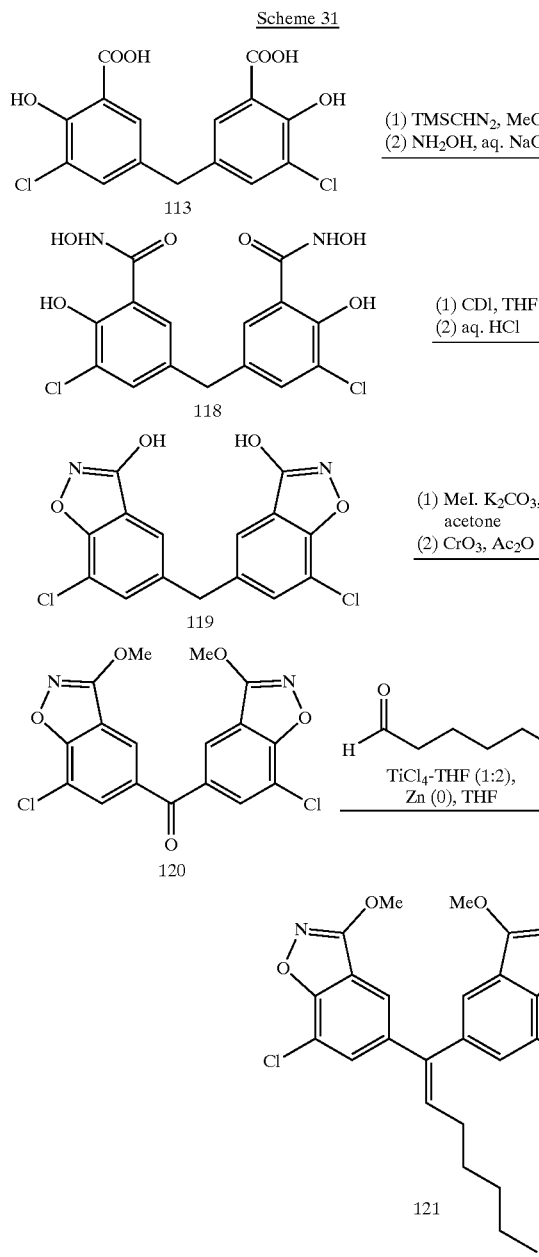

References: Hashimoto, N., Aoyama, T., Shioiri, T. "New Methods and Reagents in Organic Synthesis. 14. A Simple Efficient Preparation of Methyl Esters with Trimethylsilyl-diazomethane (TMSCHN$_2$) and Its Application to Gas Chromatographic Analysis of Fatty Acids" *Chem. Pharm. Bull.* 1981, 29, 1475–1478; Friary, R., Sunday, B. R. "A Direct Preparation of 3-hydroxy-1,2-benzisoxazoles" *J. Heterocyclic Chem.* 1979, 2516, 1277–1278.

Using the foregoing reaction schemes and other art-recognized synthetic procedures, one can prepare compounds of the invention of the formula:

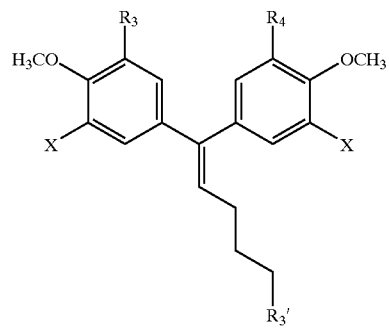

wherein X is Cl or Br and $R_3$, $R_4$, and $R_3'$ are the same and are selected from the following substituents:

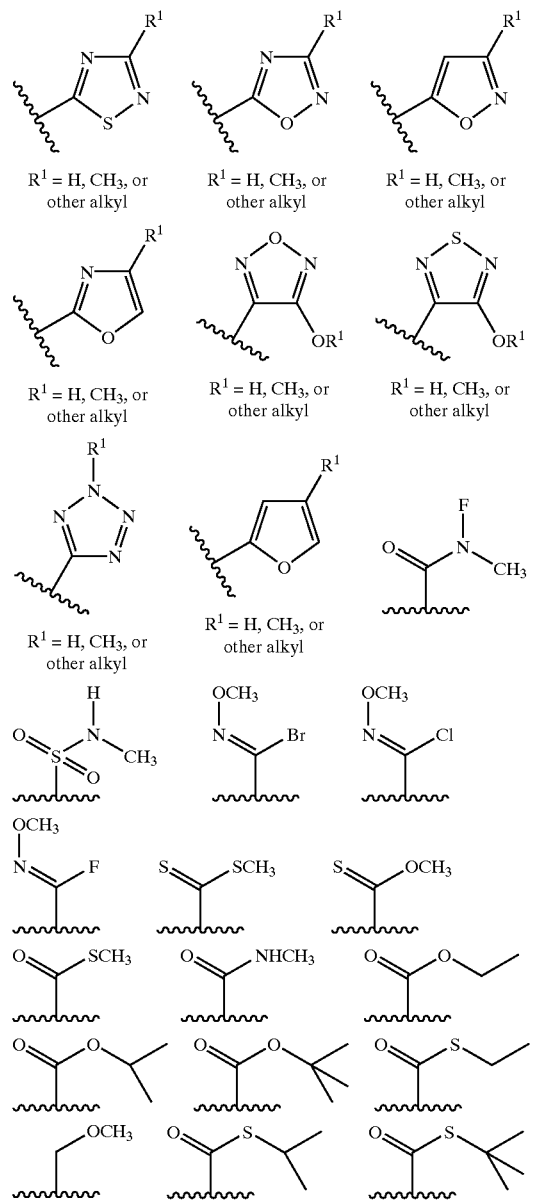

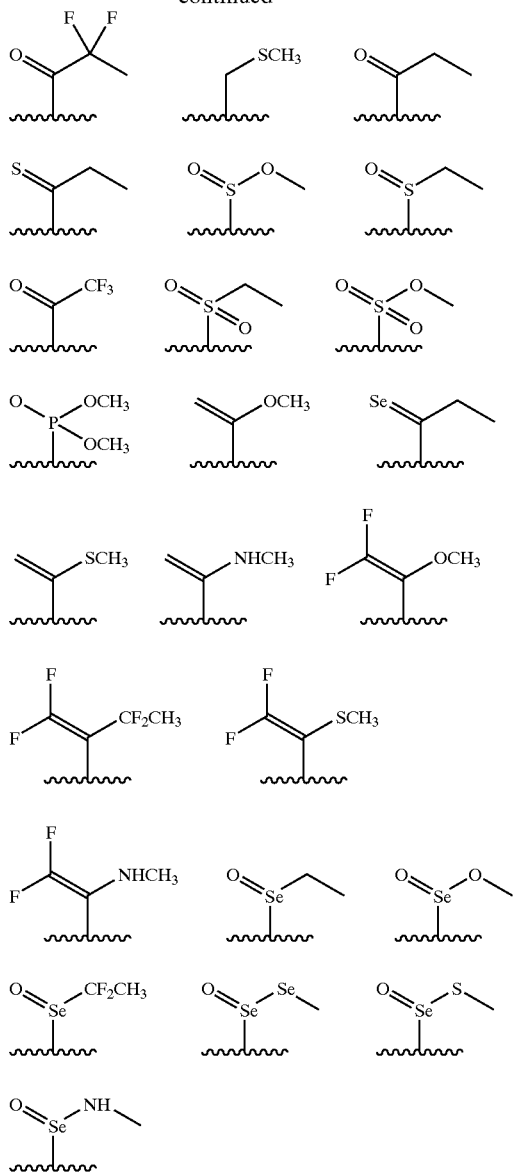
In another embodiment, there are provided fused ring analogs of the present alkenyldiarylmethane compounds, examples of which are as follows: Fused Ring Analogs ($R^1=C_1-C_4$ alkyl; $R=R_3'$ above)
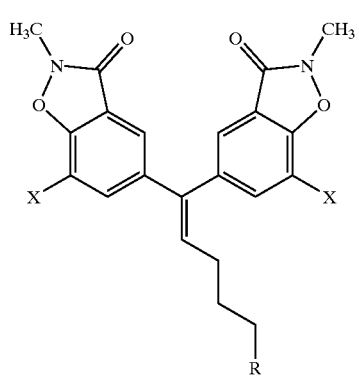
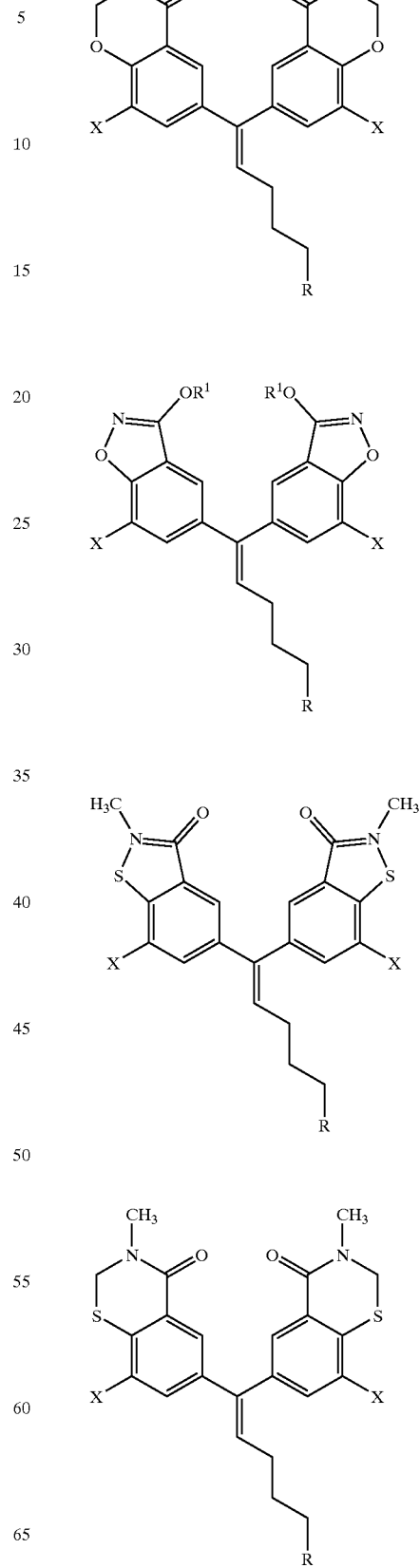
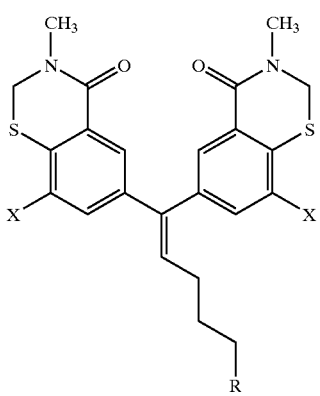

-continued

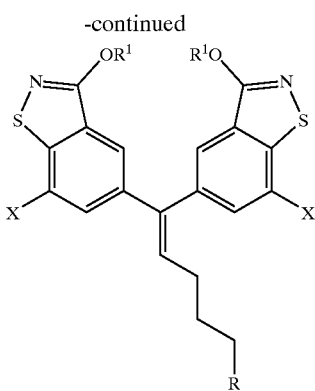

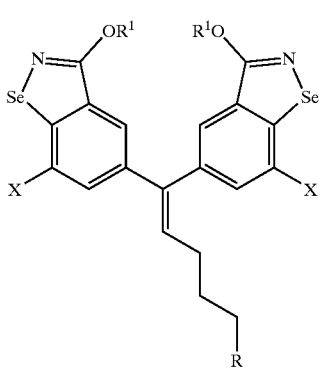

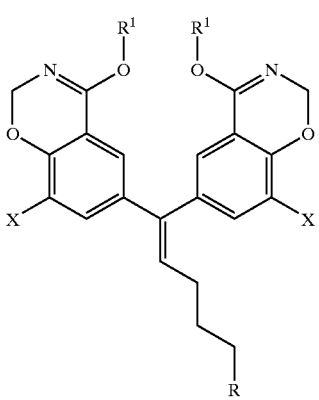

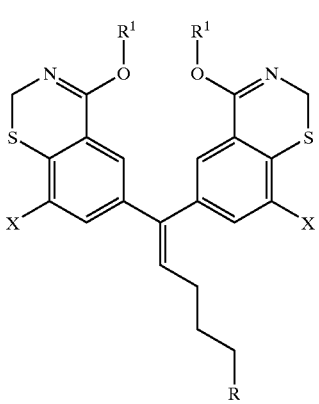

The compounds of this embodiment can be synthesized using the foregoing reaction schemes and other art-recognized synthetic procedures.

What is claimed is:

1. A compound of the formula:

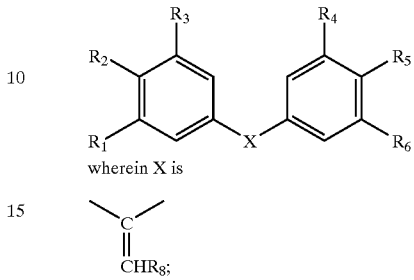

wherein X is

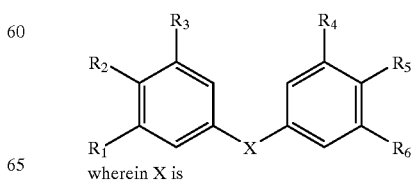

$R_1$ and $R_6$ are halo;
$R_2$ and $R_5$ are independently —$OR_{11}$;
$R_3$ and $R_4$ are —$CO_2R_{12}$;
$R_8$ is —$(CH_2)_m COOR_{14}$;
$R_{11}$, $R_{12}$, and $R_{14}$ are independently selected from the group consisting of hydrogen and —($C_1$–$C_5$) alkyl; and
m is 1–4.

2. The compound of claim 1 wherein $R_1$ and $R_6$ are independently Br or Cl, $R_2$ and $R_5$ are each —$OCH_3$, and $R_3$ and $R_4$ are each —$CO_2CH_3$.

3. A compound of the formula:

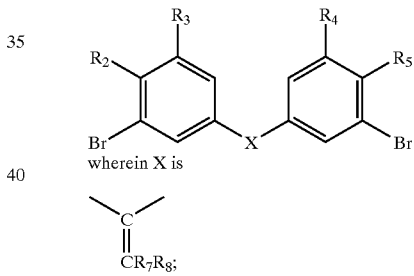

wherein X is $R_2$ and $R_5$ are independently —$OR_{11}$;
$R_3$ and $R_4$ are independently —$CO_2R_{12}$;
$R_7$ is hydrogen;
$R_8$ is —$(CH_2)_m COOR_{14}$;
$R_{11}$, $R_{12}$, and $R_{14}$ are independently selected from the group consisting of hydrogen and —($C_1$–$C_5$) alkyl; and
m is 1–3.

4. The compound of claim 3 wherein $R_2$ and $R_5$ are each —$OCH_3$, and $R_3$ and $R_4$ are each —$CO_2CH_3$.

5. A composition comprising a reverse transcriptase inhibitory effective amount of a compound of the formula:

wherein X is

-continued

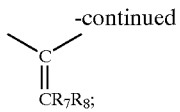

$R_1$ and $R_6$ are halo;
$R_2$ and $R_5$ are independently $-OR_{11}$;
$R_3$ and $R_4$ are $-CO_2R_{12}$;
$R_7$ is hydrogen;
$R_8$ is $-(CH_2)_mCOOR_{14}$;
$R_{11}$, $R_{12}$, and $R_{14}$ are independently selected from the group consisting of hydrogen and $-(C_1-C_5)$ alkyl; and
m is 1–4; and
a pharmaceutically acceptable carrier.

6. The composition of claim 5 wherein $R_1$ and $R_6$ are Br or Cl, $R_2$ and $R_5$ are each $-OCH_3$, and $R_3$ and $R_4$ are each $-CO_2CH_3$.

* * * * *